US010564152B2

(12) United States Patent
Burbelo

(10) Patent No.: US 10,564,152 B2
(45) Date of Patent: Feb. 18, 2020

(54) METHOD AND DEVICE FOR DETECTING ANTIGEN-SPECIFIC ANTIBODIES IN A BIOLOGICAL FLUID SAMPLE BY USING NEODYMIUM MAGNETS

(71) Applicant: The U.S.A., as represented by the Secretary, Department of Health and Human Services, Bethesda, MD (US)

(72) Inventor: Peter D. Burbelo, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/756,012

(22) PCT Filed: Aug. 8, 2016

(86) PCT No.: PCT/US2016/046037
§ 371 (c)(1),
(2) Date: Feb. 27, 2018

(87) PCT Pub. No.: WO2017/039967
PCT Pub. Date: Mar. 9, 2017

(65) Prior Publication Data
US 2018/0267031 A1 Sep. 20, 2018

Related U.S. Application Data
(60) Provisional application No. 62/212,973, filed on Sep. 1, 2015.

(51) Int. Cl.
*G01N 33/543* (2006.01)
*G01N 35/00* (2006.01)
(Continued)

(52) U.S. Cl.
CPC ..... *G01N 33/54326* (2013.01); *G01N 33/566* (2013.01); *G01N 33/582* (2013.01); *G01N 35/0098* (2013.01); *G01N 2469/20* (2013.01)

(58) Field of Classification Search
CPC ......... G01N 35/0098; G01N 33/54326; G01N 33/582; G01N 33/566
See application file for complete search history.

(56) References Cited

U.S. PATENT DOCUMENTS 5,958,706 A 9/1999 Matsunaga et al.
2003/0003516 A1* 1/2003 Robinson ........... A61K 39/0008
435/7.9
(Continued)

FOREIGN PATENT DOCUMENTS

CN 101470117 7/2009
WO WO 2007/068982 6/2007

OTHER PUBLICATIONS

Shum et al., BPIFB1 is a Lung-Specific Autoantigen Associated with Interstitial Lung Disease, 2013, Science Translational Medicine , vol. 5, Issue 206, pp. 1-10. (Year: 2013).*
(Continued)

*Primary Examiner* — Melanie Brown
(74) *Attorney, Agent, or Firm* — Klarquist Sparkman, LLP

(57) ABSTRACT

Methods for detecting antigen-specific antibodies in a biological sample are described. The disclosed methods can be used for the diagnosis of a variety of autoimmune and infectious diseases. The methods use a neodymium magnet to efficiently isolate immune complexes. The disclosed methods are rapid, highly specific and sensitive, require very small volumes of biological sample, and do not require the use of radioactivity. With these advantageous features, the disclosed methods are amendable for point-of-care testing (POCT), which is currently not available for the detection of
(Continued)

autoantibodies associated with autoimmune disease or for the detection of many pathogen-specific antibodies.

17 Claims, 13 Drawing Sheets

(51) Int. Cl.
*G01N 33/58* (2006.01)
*G01N 33/566* (2006.01)

(56) References Cited

U.S. PATENT DOCUMENTS

| | | | | |
|---|---|---|---|---|
| 2003/0040129 | A1* | 2/2003 | Shah | B01L 3/5027 506/32 |
| 2004/0157242 | A1* | 8/2004 | Ivey | C12Q 1/6883 435/6.16 |
| 2005/0277204 | A1* | 12/2005 | Hollis | C12M 47/04 436/518 |
| 2007/0259336 | A1* | 11/2007 | Burbelo | G01N 33/54306 435/5 |
| 2009/0061476 | A1* | 3/2009 | Tibbe | G01N 33/54326 435/39 |
| 2015/0051102 | A1* | 2/2015 | Fu | G01N 33/54326 506/9 |

OTHER PUBLICATIONS

Alenghat et al., "Mechanical Control of cAMP Signaling through Integrins is Mediated by the Heterotrimeric Gαs Protein," *J. Cell Biochem.*, vol. 106:529-538, 2009.

Burbelo et al., "Antibody Profiling by Luciferase Immunoprecipitation Systems (LIPS)," *JoVE* 32, 2009.

Burbelo et al., "Searching for Biomarkers: Humoral Response Profiling with Luciferase Immunoprecipitation Systems (LIPS)," *Expert Rev Proteomics* 8(3):309-316, 2011.

Burbelo and O'Hanlon, "New autoantibody detection technologies yield novel insights into autoimmune disease," *Curr Opin Rheumatol* 26(6):717-723, 2014.

Burbelo et al., "Luciferase immunoprecipitation systems for measuring antibodies in autoimmune and infectious diseases," *Transl Res* 165(2):325-335, Epub Sep. 1, 2014.

Kergaravat et al., "Electrochemical Magneto Immunosensor for the Detection of Anti-TG2 Antibody in Celiac Disease," *Biosensors and Bioelectronics*, vol. 48:203-209, 2013.

New England BioLabs (NEB) Inc., "Affinity Isolation and Purification Matricies," online at: https://www.neb.com/products/protein-expression-and-purification-technologies/magnetic-matrices-and-racks/magnetic-matrices-and-racks/affinity-isolation-and-purification-matricies, downloaded May 20, 2015 (2 pages).

Petersen and Andersen, "Simultaneous Isolation of mRNA and Native Protein from Minute Samples of Cells," *BioTechniques*, vol. 56:229-237, 2014.

Ruidíaz et al., "Development of a Sensitive Bead-Based Assay for Enhanced Monoclonal Antibody Detection," *Mater. Res. Soc. Symp. Proc.*, vol. 1346, 2011.

Sista et al., "Development of a Digital Microfluidic Platform for Point of Care Testing," *Lab Chip*, vol. 8:2091-2104, 2008.

ThermoFisher Scientific: Pierce™ Protein a Magnetic Beads, XP55310391, https://tools.thermofisher.com/content/sfs/manuals/MAN001856_Pierce_ProteinA_Mag_Bead_UG.pdf, Jan. 1, 2013 (8 pages).

* cited by examiner

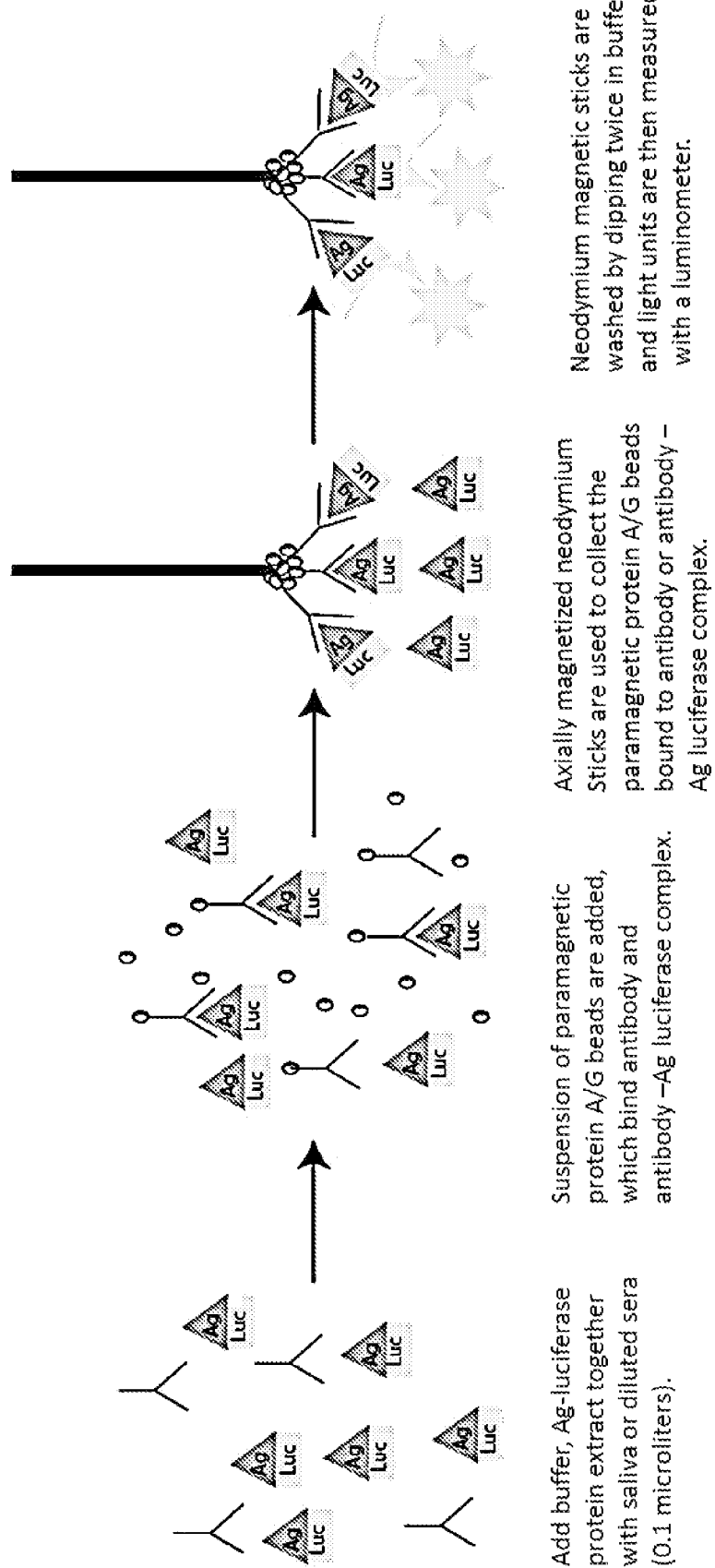

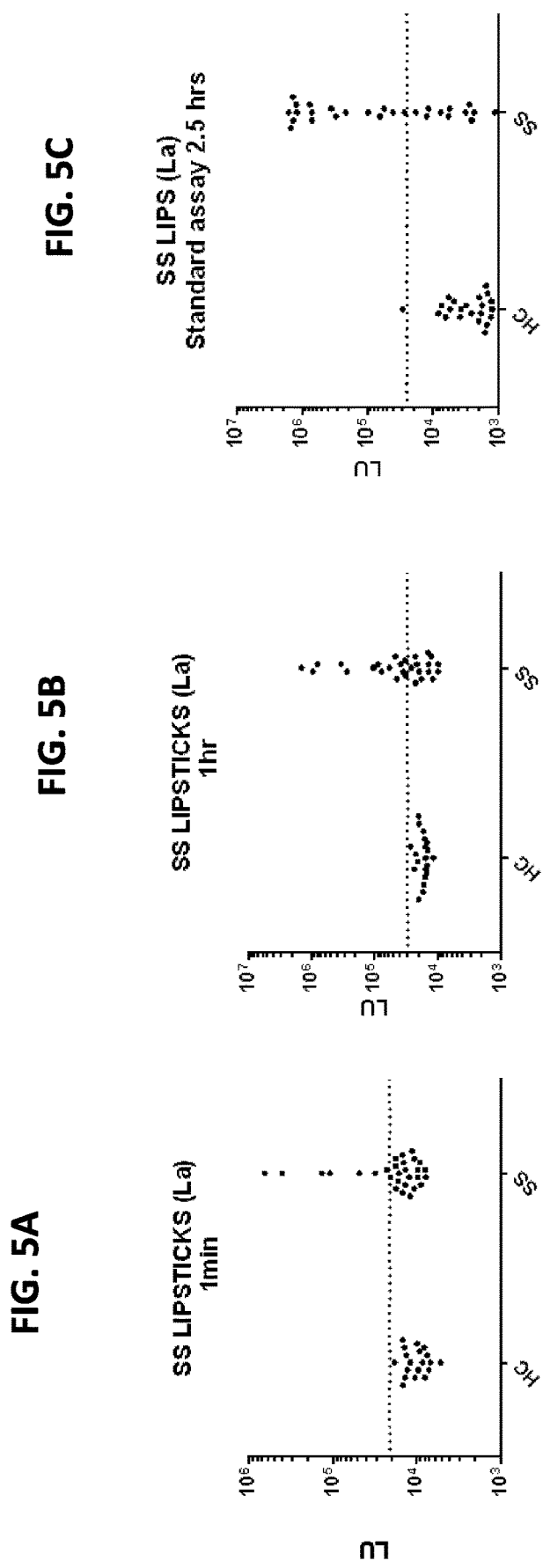

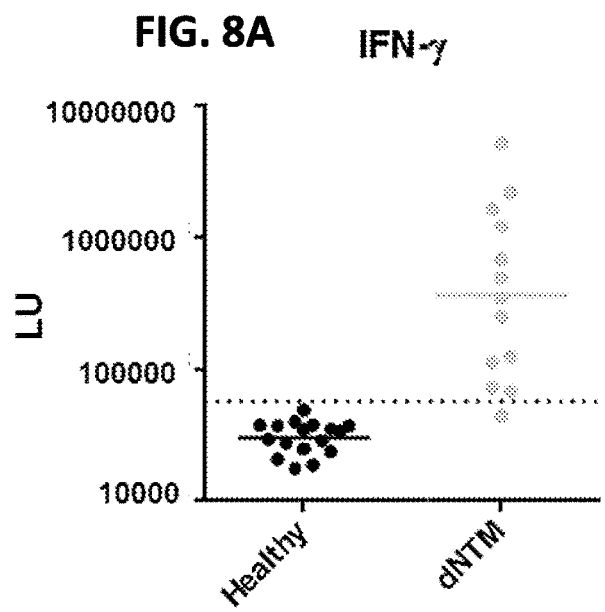
FIG. 8A IFN-γ
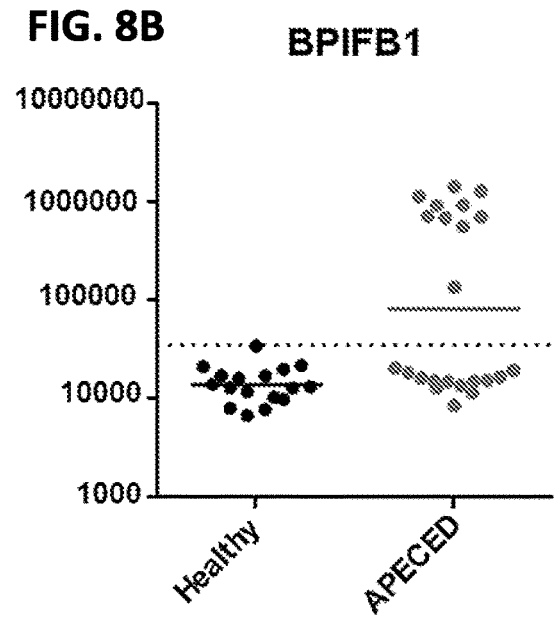
FIG. 8B BPIFB1
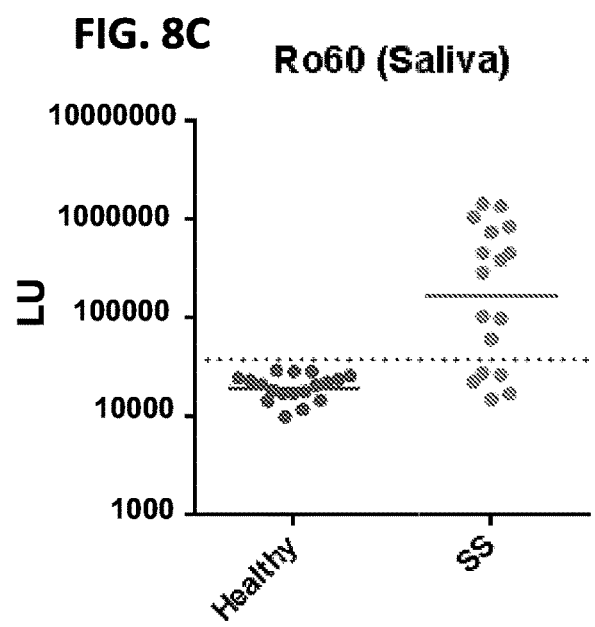
FIG. 8C Ro60 (Saliva)
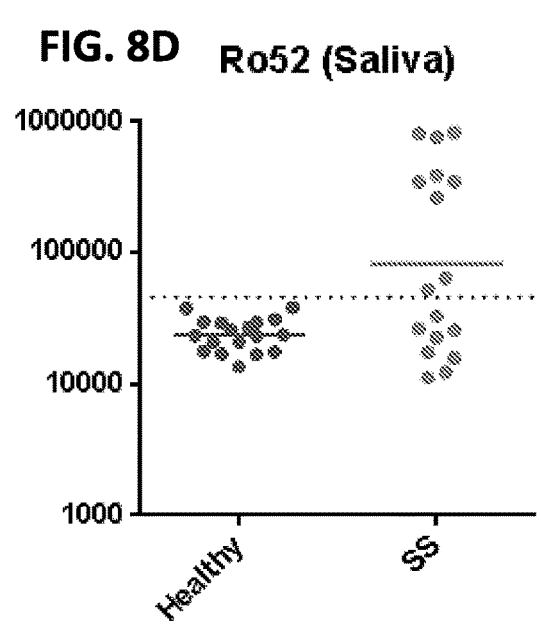
FIG. 8D Ro52 (Saliva)

METHOD AND DEVICE FOR DETECTING ANTIGEN-SPECIFIC ANTIBODIES IN A BIOLOGICAL FLUID SAMPLE BY USING NEODYMIUM MAGNETS

CROSS REFERENCE TO RELATED APPLICATIONS

This application is the U.S. National Stage of International Application No. PCT/US2016/046037, filed Aug. 8, 2016, published in English under PCT Article 21(2), which claims the benefit of U.S. Provisional Application No. 62/212,973, filed Sep. 1, 2015, which is herein incorporated by reference in its entirety.

FIELD

This disclosure concerns methods for rapidly detecting antigen-specific antibodies in biological samples using a fluid-phase immunoassay and neodymium magnets.

BACKGROUND

Point-of-care testing (POCT) is medical testing at or near the site of patient care. The driving notion behind POCT is to bring the test conveniently and immediately to the patient. This increases the likelihood that the patient, physician, and care team will receive results quickly, which allows for immediate clinical management decisions to be made.

POCT is often accomplished through the use of transportable and handheld instruments and test kits. Small bench analyzers or fixed equipment can also be used when a handheld device is not available. The goal of POCT is to collect the specimen and obtain the results in a very short period of time at or near the location of the patient so that the treatment plan can be adjusted as necessary before the patient leaves. Cheaper, faster, and smarter POCT devices have increased the use of POCT approaches by making it cost-effective for many diseases, such as diabetes, carpal tunnel syndrome and acute coronary syndrome.

Rapid point-of-care, antibody-based testing is not currently available for the diagnosis of autoimmune and most infectious diseases. For detecting autoantibodies associated with most autoimmune conditions, fluid-phase immunoprecipitation assays are necessary in order to enable detection of conformation-specific antibodies; however, these assays usually involve radioactivity, which is not feasible for point-of-care applications. Therefore, rapid, POCT diagnostic assays for diagnosis of autoimmune and infectious diseases would satisfy an important clinical need.

SUMMARY

An assay for detecting antigen-specific antibodies in biological samples that is amenable to rapid, POCT diagnostics for autoimmune and infectious disease is disclosed. The disclosed methods utilize luciferase immunoprecipitation systems (LIPS) and neodymium magnets to very rapidly detect antigen-specific antibodies with high sensitivity and specificity.

Provided herein is a method for detecting antigen-specific antibodies in a biological fluid sample. In some embodiments, the method includes providing a fusion protein comprising an antigen fused to a light-emitting protein; contacting the biological fluid sample with the fusion protein, thereby forming immune complexes if antigen-specific antibodies are present in the biological fluid sample; contacting the immune complexes with magnetic beads coated with an immunoglobulin-binding protein to form bead-bound immune complexes; isolating the bead-bound immune complexes by directly contacting the bead-bound immune complexes with a neodymium magnet; and detecting emission of light from the isolated bead-bound immune complexes.

In some examples, the biological fluid sample is a serum, plasma, blood, urine, saliva or bronchoalveolar lavage fluid sample. In some examples, the light-emitting protein comprises a fluorescent protein or a luciferase, such as a *Renilla* luciferase, a *Gaussia* luciferase, a modified (optimized) *Oplophorus gracilirostris* luciferase (for example, NANO-LUC™), a firefly luciferase or a bacterial luciferase. In some examples, the immunoglobulin-binding protein is Protein A, Protein G, Protein A/G, Protein L or a secondary immunoglobulin molecule.

In some examples, the antibodies are autoantibodies. In other examples, the antibodies are pathogen-specific antibodies.

Also provided herein are methods of diagnosing a subject as having an autoimmune disease by performing the disclosed methods to detect autoantibodies in a biological sample from the subject that are indicative of the autoimmune disease.

Further provided herein are methods of diagnosing a subject as infected with a pathogen by performing the disclosed methods to detect pathogen-specific antibodies in a biological sample from the subject.

Also provided herein is a device for detecting antigen-specific antibodies in a plurality of biological fluid samples simultaneously, according to the methods disclosed herein. In some embodiments, the device includes a first solid support for housing a plurality of biological fluid samples and a second solid support having a plurality of neodymium magnets affixed thereto.

The foregoing and other objects, features, and advantages of the invention will become more apparent from the following detailed description, which proceeds with reference to the accompanying figures.

BRIEF DESCRIPTION OF THE DRAWINGS

FIG. 1 is a schematic depiction of the LIPSTICKS method disclosed herein. Only four steps are required for 1 minute antibody detection by LIPSTICKS: Recombinant luciferase antigen fusion proteins (Ag-luciferase) are mixed together with diluted biological sample, such as sera or saliva; paramagnetic protein A/G-coated beads are added and bind antibody-antigen complexes; neodymium magnets collect the paramagnetic protein A/C-immune complexes and are briefly washed; and magnet-bound immune complexes are placed into tubes containing luciferase substrate and emitted light is measured with a tube or hand-held luminometer.

(FIG. 2A) Increasing the volume (μl) of paramagnetic beads resulted in a better LU signal. (FIG. 2B) A range of sera between 0.001 μl and 4 μl was tested. The results showed that 0.1 μl of sera provided the optimum signal. (FIG. 2C) Increasing the amount of Ruc-Ro52 extract as input improved the LU signal. (FIG. 2D) Lengthening the time of incubation from 30 seconds to 4 minutes also increased the Ro52 autoantibody signal for the Sjögren's syndrome subject sample.

(FIG. 3A) The LIPSTICK one minute assay results are shown. (FIG. 3B) For comparison, the data obtained from the standard 2.5 hour LIPS test performed in 96 well, microtiter and filter plate format is also presented. The cut-off values (dotted line) for each assay are based on the mean plus three standard deviations of the HC group.

FIGS. 5A-5C are a series of graphs comparing the LIPSTICK and LIPS assays for detection of La autoantibodies. A sample set of 20 HC and 28 SS patients was examined for La autoantibodies. (FIG. 5A) Results from the LIPSTICKS one minute assay for detection of La autoantibodies are shown. (FIG. 5B) A prolonged, one hour LIPSTICK assay for detection of La autoantibodies was also tested. (FIG. 5C) For comparison, results from the standard 2.5-hour LIPS assay are shown. The cut-off values used to determine diagnostic performance are indicated by the dotted line. The one minute LIPSTICK test yielded 25% sensitivity (100% specificity); the one hour LIPSTICK test yielded 53% sensitivity (100% specificity); and the standard 2.5 hour LIPS test yielded 61% sensitivity (98% specificity) for the detection of La autoantibodies. The clinical ELISA test shows only 45% sensitivity.

(FIG. 7A) Antibody detection by LIPSTICKS using luciferase-HIV p24 extract with log-dilutions of sera from HIV negative and HIV positive individuals reveals that 0.1 µl of sera produces the highest signal to noise ratio. (FIG. 7B) Increasing the amount of luciferase-HIV p24 antigen produces a linear increase in LU for both the HIV negative and HIV positive samples. (FIG. 7C) HIV reverse transcriptase antibody detection in a cohort of HIV negative and HIV positive individuals. The geometric mean in each group is shown by the horizontal bar and the cut-off value for seropositivity is shown by the dotted line. (FIG. 7D) Epstein-Barr virus (EBV) negative and EBV positive individuals were tested for antibodies with an EBV Epstein-Barr nuclear antigen (EBNA) luciferase antigen fusion. The geometric means and the cut-off value are shown as in FIG. 7C.

FIGS. 8A-8F are a series of graphs showing LIPSTICKS autoantibody detection for autoimmune disease diagnosis. (FIG. 8A) Evaluation of autoantibodies against IFN-γ in the sera of controls and subjects with disseminated non-tuberculosis infection demonstrated a diagnostic performance of 95% sensitivity and 100% specificity. (FIG. 8B) Autoantibodies against BPI fold containing family B, member 1 (BPIFB1) in the sera of control subjects and subjects with autoimmune polyendocrinopathy-candidiasis-ectodermal dystrophy (APECED). Only a subset of APECED patients had BPIFB1 autoantibodies and LIPSTICKS demonstrated a diagnostic performance of 95% sensitivity and 100% specificity. (FIG. 8C) Ro60 and (FIG. 8D) Ro52 autoantibodies detected in the saliva of healthy controls and patients with Sjögren's syndrome. (FIG. 8E) Serum autoantibodies against Ro60 in healthy controls and patients with Sjögren's syndrome. (FIG. 8F) Comparison of Ro52 serum autoantibodies detected by tube luminometer vs. a hand held luminometer.

(FIG. 9A) Varying the amount of protein A/G coated beads produced an increase in LU for both the HIV negative and HIV positive samples with the luciferase-HIV p24 antigen. One µl of beads was chosen for testing. (FIG. 9B) Lengthening the time of incubation from 1 minute to 10 minutes also modestly increased the LU signal for p24 antibodies of the HIV seropositive sample.

DETAILED DESCRIPTION

I. Abbreviations

Figure 2A:
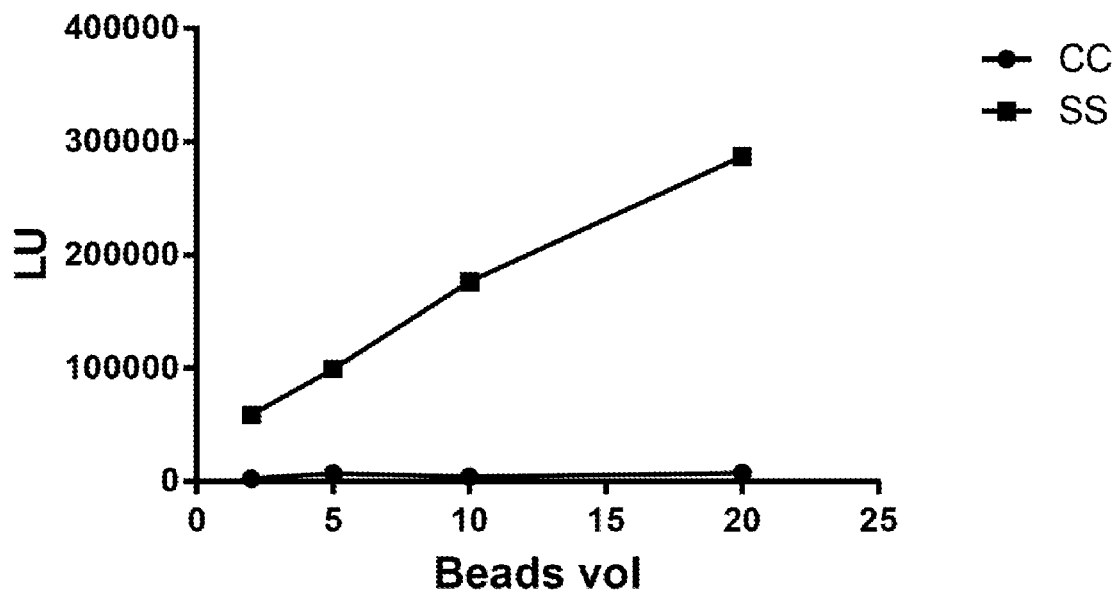
FIGS. 2A-2D are a series of graphs showing the results of testing various LIPSTICK immunoassay parameters. In each experiment, sera from a representative control subject (closed circle) and a representative Sjögren's syndrome patient (closed square) were tested with *Renilla* luciferase fused to Ro52 (Ruc-Ro52). The resulting light units (LU) are shown on the Y-axis.

APECED autoimmune polyendocrinopathy-candidiasis-ectodermal dystrophy
BPIFB1 BPI fold containing family B, member 1
dNTM disseminated non-tuberculosis mycobacterial
EBNA Epstein-Barr nuclear antigen
EBV Epstein-Barr virus
ELISA enzyme linked immunosorbent assay
HC healthy control
HIV human immunodeficiency virus
LIPS luciferase immunoprecipitation systems
LU luciferase unit
NPHV non-primate hepacivirus
POC point-of-care POCT point-of-care testing
RT reverse transcriptase
SS Sjögren's syndrome
VCA viral capsid antigen

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad of immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibodies" includes intact immunoglobulins as well as a number of well-characterized fragments. For instance, Fabs, Fvs, and single-chain Fvs (scFvs) that bind to target protein (or epitope within a protein or fusion protein) would also be specific binding agents for that protein (or epitope). These antibody fragments are defined as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibodies for use in the methods of this disclosure can be monoclonal or polyclonal, and for example specifically bind a target such as the target antigen. Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Antigen-specific: As used herein, an "antigen-specific" antibody is an antibody that was elicited (produced and/or activated) in response to a particular antigen. An "antigen-specific" antibody is capable of binding to the antigen, typically with high affinity.

Autoantibody: An antibody produced in an organism that is directed against a constituent of the organism's own tissue (i.e. an antibody specific for a self-antigen).

Autoimmune disease: A disease arising from an abnormal immune response directed against proteins and tissues normally present in the body. There are currently more than 80 defined types of autoimmune diseases.

Contacting: Placement in direct physical association. In the context of the present disclosure, "directly contacting" bead-bound immune complexes with a neodymium magnet requires that the bead-bound immune complexes and neodymium magnet make direct physical contact without any intervening materials or substances. Thus, directly contacting the bead-bound immune complexes and neodymium magnet excludes instances in which a magnet is placed outside of a tube, container, culture vessel or other structure to concentrate bead-bound immune complexes within the tube, container, culture vessel or other structure.

Fluorescent protein: A protein that emits light of a certain wavelength when exposed to a particular wavelength of light. Fluorescent proteins include, but are not limited to, green fluorescent proteins, blue fluorescent proteins, cyan fluorescent proteins, yellow fluorescent proteins, orange fluorescent proteins, red fluorescent proteins and modified versions thereof.

Fusion protein: A protein containing amino acid sequence from at least two different (heterologous) proteins or peptides. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis.

Helminth: A parasitic worm, such as a fluke, tapeworm or nematode.

Heterologous: A heterologous protein or polypeptide refers to a protein or polypeptide derived from a different source or species.

Human immunodeficiency virus (HIV): A retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by HIV, as determined by antibody or western blot studies. Laboratory findings associated with this disease include a progressive decline in T cells. HIV includes HIV type 1 (HIV-1) and HIV type 2 (HIV-2).

Immune complex: A protein complex that comprises an antibody bound to an antigen. In the context of the present disclosure, an "immune complex" comprises (1) a fusion protein, which is made up of a selected antigen fused to a light-emitting protein; and (2) an antibody that specifically binds the antigen. A bead-bound immune complex is an immune complex that is further bound to at least one bead (such as a magnetic bead) that is coated with an immunoglobulin-binding protein. The immunoglobulin-binding proteins on the surface of the bead bind to the antibody present in the immune complex.

Immunoglobulin-binding protein: Any protein that specifically binds an immunoglobulin molecule. Examples of immunoglobulin-binding molecules include, but are not limited to, Protein A, Protein G, Protein A/G, Protein L and secondary immunoglobulins (for example, anti-IgG, anti-IgM, anti-IgA, anti-IgE or anti-IgD antibodies).

Isolated: An "isolated" biological component (such as a nucleic acid molecule, protein, or cell) has been substantially separated or purified away from other biological components in the cell, blood or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Light-emitting protein: Any protein that is capable of emitting light or inducing the emission of light by acting on a particular substrate. Light-emitting proteins include, for example, fluorescent proteins and bioluminescent proteins. Fluorescent proteins include, for example, green fluorescent proteins and variants thereof (including blue, cyan, yellow, orange and red fluorescent proteins) and phycobiliproteins, such as B-phycoerythrin (B-PE), R-phycoerythrin (R-PE) and allophycocyanin (APC). Bioluminescent proteins include, for example, aequorin and luciferase (which acts on the substrate luciferin to emit light).

Linker: One or more nucleotides or amino acids that serve as a spacer between two molecules, such as between two nucleic acid molecules or two peptides (such as in a fusion protein).

Luciferin: A light-emitting compound found in organisms that generate bioluminescence. Luciferins are small molecule substrates that undergo an enzyme-catalyzed oxidation and the resulting excited state intermediate emits lights upon decaying to its ground state.

Luciferase: An oxidative enzyme that generates light by reacting with luciferin. Commonly used luciferase proteins include *Renilla* luciferase, *Gaussia* luciferase, *Oplophorus gracilirostris* (deep sea shrimp) luciferase (a modified version with increased stability, NANOLUC™, is commercially available), firefly luciferase and bacterial luciferase. Exemplary luciferases and the substrates they act upon are shown in the table below.

| Organism | Luciferase | Substrate |
|---|---|---|
| *Photinus pyralis* | North American firefly luciferase | D-luciferin |
| *Luciola cruciata* | Japanese firefly (Genji-botaru) luciferase | D-luciferin |
| *Luciola italica* | Italian firefly Luciferase | D-luciferin |
| *Luciola lateralis* | Japanese firefly (Heike) luciferase | D-luciferin |
| *Luciola mingrelica* | East European firefly luciferase | D-luciferin |
| *Photuris pennsylvanica* | Pennsylvania firefly luciferase | D-luciferin |
| *Pyrophorus plagiophthalamus* | Click beetle luciferase | D-luciferin |
| *Phrixothrix hirtus* | Railroad worm luciferase | D-luciferin |
| *Renilla reniformis* | *Renilla* luciferase | Coelenterazine |
| | Rluc8 (mutant of *Renilla* luciferase) | Coelenterazine |
| | Green *Renilla* luciferase | Coelenterazine |
| *Gaussia princeps* | *Gaussia* luciferase | Coelenterazine |
| | *Gaussia*-Dura luciferase | Coelenterazine |
| *Cypridina noctiluca* | *Cypridina* luciferase | Vargulin/*Cypridina* luciferin |
| *Cypridina hilgendorfii* | *Cypridina* (*Vargula*) luciferase | Vargulin/*Cypridina* luciferin |
| *Metridia longa* | *Metridia* luciferase | Coelenterazine |
| *Oplophorus gracilorostris* | NANOLUC ™ (optimized) | Furimazine (Nano-Glo ™ assay substrate) |

Neodymium magnet: A type of rare-earth magnet made from an alloy of neodymium, iron and boron. Neodymium magnets are the strongest type of permanent magnet that is commercially available.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pathogen: A biological agent that causes disease or illness to its host. Pathogens include, for example, bacteria, viruses, fungi, helminths, protozoa and other parasites. Pathogens can also be referred to as infectious agents.

Plurality: Any number that is more than one. In some embodiments herein, a "plurality" means at least 6, at least 12, at least 24, at least 48, at least 96, or at least 384.

Protein A: An immunoglobulin-binding protein. Protein A is a 42 kDa surface protein originally found in the cell wall of the bacterium *Staphylococcus aureus*. The presence of five immunoglobulin-binding domains allows Protein A to bind immunoglobulin molecules. Protein A binds with high affinity to the Fc portion of human IgG, $IgG_1$, $IgG_2$, and $IgG_4$, and also binds with lesser affinity to $IgG_3$, IgM, IgE and IgA (including $IgA_1$ and $IgA_2$). Protein A also binds to immunoglobulin molecules from a variety of different species.

Protein G: An immunoglobulin-binding protein expressed in group C and G Streptococcal bacteria. Protein G can binds strongly to human IgG, $IgG_1$, $IgG_2$, $IgG_3$, and $IgG_4$, as well as IgG molecules from a variety of different species. When used for purification of antibodies, a recombinant form of Protein G lacking the albumin binding domain is used.

Protein A/G: A recombinant fusion protein that combines immunoglobulin binding domains of Protein A and Protein G. Protein A/G contains four Fc binding domains from Protein A and two Fc binding domains from Protein G. Protein A/G binds with high affinity to all subclasses of human IgG, and also binds to human IgA, IgE and IgM (and to a lesser extent IgD), as well immunoglobulin molecules from a variety of different species.

Protein L: An immunoglobulin-binding protein first isolated from the surface of the bacterial species *Peptostreptococcus magnus*. Protein L binds to the kappa light chain of immunoglobulin molecules. Protein L binds strongly to all subclasses of human IgG, IgM, IgA, IgE, IgD, as well as scFv and Fab fragments. Protein L can also bind to immunoglobulin molecules of several non-human species.

Protozoa: Unicellular eukaryotic organisms. Some protozoa are parasites that cause disease in humans, for example, malaria (*Plasmodium* species), amoebiasis (*Entamoeba* species), giardiasis (*Giardia lamblia*), toxoplasmosis (*Toxoplasma gondii*), cryptosporidiosis (*Cryptosporidium* species), trichomoniasis (*Trichomonas vaginalis*), Chagas disease (*Trypanosoma cruzi*), Leishmaniasis (*Leishmania* species), sleeping sickness (*Trypanosoma brucei*), amoebic dysentery (*Entamoeba histolytica*), acanthamoeba eeratitis (*Acanthamoeba* species), and primary amoebic meningoencephalitis (*Naegleria fowleri*).

Recombinant: A recombinant nucleic acid molecule or protein is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids and proteins that have been altered solely by addition, substitution, or deletion of a portion of the natural nucleic acid molecule or protein.

Sample: Refers to any biological or environmental sample. A biological sample is a sample obtained from a subject (such as a human or veterinary subject). In particular examples, the biological sample is a biological fluid sample. Biological fluid samples from a subject include, but are not limited to, serum, blood, plasma, urine, saliva, cerebral spinal fluid (CSF), bronchoalveolar lavage fluid or other bodily fluid.

Sjögren's syndrome: An autoimmune disorder characterized by immune cells that attack and destroy the glands that produce tears and saliva. Sjögren's syndrome is not life-threatening or life-shortening, but can significantly reduce quality of life. The hallmark symptoms of the disorder are dry mouth and dry eyes. Sjögren's syndrome may also cause skin, nose and vaginal dryness, and can affect other organs of the body including the kidneys, blood vessels, lungs, liver, pancreas and brain. Sjögren's syndrome affects 1-4 million people in the United States, with women being nine times more likely to develop the disease. The majority of Sjögren's sufferers are at least 40 years old at the time of diagnosis. Sjögren's syndrome can occur as a primary condition or as a secondary disorder in association with a connective tissue disease, such as systemic lupus erythematosus ("lupus"), rheumatoid arthritis or scleroderma.

Subject: Living multi-cellular vertebrate organisms, a category that includes human and non-human mammals.

Synthetic: Produced by artificial means in a laboratory, for example a synthetic nucleic acid can be chemically synthesized in a laboratory.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

There is great interest in point-of-care clinical immunoassays for the diagnosis of infectious and autoimmune diseases. Lateral flow immunoassays have been utilized as one approach to produce rapid qualitative, positive/negative diagnostic results for detecting antigens and for antibody-based detection of selected infectious agents including HIV and hepatitis C virus (Smith et al., *Antivir Ther* 17(7 Pt B):1409-1413, 2012; Yager et al., *Annu Rev Biomed Eng* 10:107-144, 2008). Other technologies, such as miniaturized ELISAs (mChip) have also been employed for the rapid, serological diagnosis of HIV and syphilis infections (Chin et al., *Nat Med* 17(8):1015-1019, 2011; Laksanasopin et al., *Sci Transl Med* 7(273):273 rel, 2015). However, only a few rapid immunoassays, such as for celiac disease (Bienvenu et al., *BMC Gastroenterol* 14:186, 2014) and vasculitis (Offermann et al., *J Immunol Methods* 403(1-2):1-6, 2014) have been reported for the detection of autoantibodies associated with autoimmune diseases.

Fluid-phase immunoprecipitation assays show the highest sensitivity for the diagnosis of autoimmune diseases due to their ability to effectively detect conformational autoantibodies (Burbelo et al., *Transl Res* 165(2):325-335, 2015; Liu and Eisenbarth, *Clin Immunol* 125(2):120-126, 2007). However, these assays are often not feasible for point-of-care applications due to the usual requirement of radioactivity. One alternative fluid phase immunoassay, luciferase immunoprecipitation systems (LIPS), employs light-emitting luciferase antigen fusions for detecting antigen-specific antibodies (Burbelo et al., *Transl Res* 165(2):325-335, 2015). In LIPS, if antibodies are present, they bind to light-emitting antigens and the antigen-antibody complexes are then captured by protein A/G beads, washed and luciferase activity is measured. The amount of light produced is proportional to the amount of antibody present. Several key advantages of LIPS are the high signal to noise detection, the ability to efficiently detect conformational epitopes and the ability to use antigen mixtures. Although a number of formats including tube (Burbelo et al., *BMC Biotechnol* 5:22, 2005), plate (Burbelo et al., *J Vis Exp* 32:1549, 2009) and microfluidic (Zubair et al., *Biomed Microdevices* 13(6):1053-1062, 2011) formats exist for LIPS, the development of a rapid format that requires limited assay manipulation and liquid handling is highly desirable.

Disclosed herein is the development of an immunoassay ("LIPSTICK") for measuring antibodies by employing neodymium magnetic sticks in combination with LIPS (FIG. 1). In this method, cell extracts of light-emitting protein-antigen fusions and a biological fluid sample, such as a serum sample, are incubated together, which is then followed by the addition of paramagnetic beads coated with an immunoglobulin-binding protein, such as protein A/G. Next axially, magnetized neodymium magnets are used to directly capture bead-bound, antibody-antigen complexes. The magnets are washed twice in buffer, and the antigen-specific antibody present in the sample is quantified. For example, if a *Renilla* luciferase-antigen fusion protein is used as the light-emitting protein, the antibody is quantified by placing the magnet in a tube of coelenterazine and the luciferase activity can be measured, for example, in a tube luminometer.

Provided herein is a method for detecting antigen-specific antibodies in a biological fluid sample. The method includes providing a fusion protein comprising an antigen fused to a light-emitting protein; contacting the biological fluid sample with the fusion protein, thereby forming immune complexes if antigen-specific antibodies are present in the biological fluid sample; contacting the immune complexes with magnetic beads coated with an immunoglobulin-binding protein to form bead-bound immune complexes; isolating the bead-bound immune complexes by directly contacting the bead-bound immune complexes with a neodymium magnet; and detecting emission of light from the isolated bead-bound immune complexes. A key feature of this assay is the direct contact of the neodymium magnet with bead-bound immune complexes in the biological fluid sample. This differs from other immunoassays involving the use of magnetic beads in which magnets are used on the exterior of a tube, culture plate or other vessel as a means to concentrate bead-bound complexes within the vessel, while the remaining fluid within the vessel is removed. Directly contacting the bead-bound immune complexes with the neodymium magnet significantly increases the rapidity of the assay, in which only a simple and short wash step is required.

Although antibodies present in the biological sample that are not specific for the antigen of interest may also bind the magnetic beads coated with the immunoglobulin-binding protein, this will not interfere with the readout of the assay since these antibodies will not bind the fusion protein and therefore will not emit a detectable signal.

The biological fluid sample can be any biological fluid in which antibodies can be present. In some embodiments, the biological fluid sample is a serum, plasma, blood, urine, saliva or bronchoalveolar lavage fluid sample. The disclosed methods are capable of detecting antigen-specific antibodies in very small sample volumes. In some examples, the total volume of the biological fluid sample is no more than 10, no more than 8, no more than 6, no more than 4, no more than 2, no more than 1, no more than 0.5, no more than 0.25, no more than 0.1, no more than 0.05, no more than 0.025, or no more than 0.01 µL. The biological fluid sample can be diluted in an appropriate buffer as needed to carry out the assay. In some instances, the biological sample is diluted prior to use in the LIPSTICKS assay, such as diluted 1:2, 1:3, 1:4, 1:5, 1:6, 1:7, 1:8, 1:9 or 1:10. In other instances, the biological sample is used undiluted. In one non-limiting embodiment, the biological sample is an undiluted saliva sample and the total volume of the saliva sample is no more than 10 µL.

In some embodiments, the light-emitting protein comprises a luciferase. In some examples, the luciferase is *Renilla* luciferase, *Gaussia* luciferase, firefly luciferase or a bacterial luciferase. When a luciferase is used as the light-emitting protein, luciferase activity is used as a measure of the quantity of antigen-specific antibody present in the sample. Luciferase activity is measured by contacting the magnet bound to bead-bound immune complexes with an appropriate luciferase substrate (such as luciferin or coelenterazine) and measuring the emission of light, for example with a luminometer.

In other embodiments, the light-emitting protein comprises a fluorescent protein, such as a green fluorescent protein, a blue fluorescent protein, a cyan fluorescent protein, a yellow fluorescent protein, an orange fluorescent protein, a red fluorescent protein, or a modified version thereof, or a phycobiliprotein, such as B-phycoerythrin (B-PE), R-phycoerythrin (R-PE) or allophycocyanin (APC). When a fluorescent protein is used as the light-emitting protein, fluorescence intensity is used as a measure of the quantity of antigen-specific antibody present in the sample. Fluorescence intensity is measured by exposing the magnet bound to bead-bound immune complexes with an appropriate wavelength of light and measuring light emission.

In some embodiments, the immunoglobulin-binding protein comprises Protein A, Protein G, Protein A/G, or Protein L. In particular examples, the immunoglobulin-binding protein comprises Protein A/G. In other embodiments, the immunoglobulin-binding protein comprises a secondary antibody, such as anti-IgG antibody, anti-IgM antibody, anti-IgA antibody, anti-IgE antibody, anti-IgD antibody, or any combination or two or more thereof. In particular examples, the secondary antibody comprises anti-IgG antibody. One of skill in the art can select an appropriate immunoglobulin-binding protein based, for example, on the particular immunoglobulin binding properties of each protein/antibody.

The neodymium magnet used in the disclosed methods can be any size or shape suitable for binding immune complexes within a tube, multi-well plate, culture vessel or other container. Generally, the magnets are rod-shaped and narrow in diameter, such as less than about ¼ inch in diameter (less than about 6.35 mm in diameter). In some embodiments, the magnet is rod-shaped and has a diameter of about $\frac{1}{32}$ inch to about ¼ inch (about 0.79 mm to about 6.35 mm), such as about $\frac{1}{16}$ inch to about $\frac{3}{16}$ inch (about 1.59 mm to about 4.76 mm). In particular non-limiting examples, the magnet is rod-shaped and has a diameter of about $\frac{1}{32}$ inch (0.79 mm), about $\frac{1}{16}$ inch (1.59 mm), about ⅛ inch (3.18 mm), about $\frac{3}{16}$ inch (4.76 mm), or about ¼ inch (6.35 mm). In particular non-limiting examples, the magnet is rod-shaped and has a diameter of about ⅛ inch (3.18 mm). In other examples, particularly when the method is carried out using a high-throughput device (for example, using a multi-well plate), the magnet is very thin, such as less than about 1 mm in diameter. In non-limiting examples, the magnet is about 0.9 mm, about 0.8 mm, about 0.7 mm, about 0.6 mm, about 0.5 mm, about 0.4 mm, about 0.3 mm, about 0.2 mm or about 0.1 mm in diameter.

An important advantage of the disclosed methods compared to prior art methods for detecting antigen-specific antibodies in a biological sample is the rapid nature of the assay, with each step requiring little time to achieve high sensitivity and specificity. Thus, in some embodiments, the step of contacting the biological fluid sample with the fusion protein (to form immune complexes if antigen-specific antibodies are present in the biological fluid sample) is performed for a maximum of 4 minutes; a maximum of 3 minutes; a maximum of 2 minutes; a maximum of 1 minute; a minimum of 10 seconds to a maximum of 4 minutes; a minimum of 20 seconds to a maximum of 3 minutes; or a minimum of 30 seconds to a maximum of 2 minutes. In some instances, the step of contacting the biological fluid sample with the fusion protein (to form immune complexes if antigen-specific antibodies are present in the biological fluid sample) is performed for a slightly longer period as needed (depending upon, for example, the affinity of the antibodies to be detected), such as for a maximum of about 3 hours, 2 hours, 1 hour, 30 minutes, 25 minutes, 20 minutes, 15 minutes, 10 minutes, 9 minutes, 8 minutes, 7 minutes, 6 minutes or 5 minutes.

In some embodiments, the step of contacting the immune complexes with magnetic beads coated with an immunoglobulin-binding protein to form bead-bound immune complexes is performed for a maximum of 6 minutes; a maximum of 5 minutes; a maximum of 4 minutes; a maximum of 3 minutes; a maximum of 2 minutes; a minimum of 10 seconds to a maximum of 6 minutes; a minimum of 20 seconds to a maximum of 5 minutes; or a minimum of 30 seconds to a maximum of 4 minutes. In some instances, the step of contacting the immune complexes with magnetic beads coated with an immunoglobulin-binding protein to form bead-bound immune complexes is performed for a slightly longer period as needed, such as for a maximum of about 3 hours, 2 hours, 1 hour, 30 minutes, 25 minutes, 20 minutes, 15 minutes, 10 minutes, 9 minutes, 8 minutes or 7 minutes.

In some embodiments, the step of isolating the bead-bound immune complexes by directly contacting the bead-bound immune complexes with a neodymium magnet is performed for a maximum of 5 seconds, 10 seconds, 15 seconds, 20 seconds, 30 seconds, 45 seconds, 1 minute or two minutes.

In some embodiments, the steps of contacting the biological fluid sample with the fusion protein, thereby forming immune complexes if antigen-specific antibodies are present in the biological fluid sample; contacting the immune complexes with magnetic beads coated with an immunoglobulin-binding protein to form bead-bound immune complexes; isolating the bead-bound immune complexes by directly contacting the bead-bound immune complexes with a neodymium magnet; and detecting emission of light from the isolated bead-bound immune complexes are carried out in a total of less than 10 minutes, less than 9 minutes, less than 8 minutes, less than 7 minutes, less than 6 minutes, less than 5 minutes, less than 4 minutes, or less than 3 minutes.

The emission of light can be detected using any means known in the art. In some embodiments, the emission of light is detected using a luminometer, such as a hand-held luminometer.

The disclosed methods can be used to detect, for example, autoantibodies or pathogen-specific antibodies.

In some embodiments, the autoantibodies are indicative of any one of a number of autoimmune diseases, such as but not limited to, Sjögren's syndrome, type 1 diabetes, rheumatoid arthritis, systemic lupus erythematosus, celiac disease, myasthenia gravis, Hashimoto's thyroiditis, Graves' disease, autoimmune polyendocrinopathy-candidiasis-ectodermal dystrophy (APECED), disseminated non-tuberculosis mycobacterial (dNTM) infection, or any other autoimmune disease listed in section IV or known in the art. In some examples, the autoantibodies associated with patients with Sjögren's syndrome and several other rheumatologic diseases include antibodies against Ro52, Ro60 or La. In some examples, the autoantibodies are indicative of dNTM infection, such as autoantibodies specific for interferon-γ. In some examples, the autoantibodies are associated with APECED including autoantibodies against BPI fold containing family B, member 1 (BPIFB1) Autoimmune diseases as well as autoantibodies that are indicative of particular autoimmune diseases are discussed further in section IV.

In some embodiments in which the antibodies are pathogen-specific antibodies, the pathogen is a viral pathogen, a bacterial pathogen, a fungal pathogen, a parasitic helminth, or a parasitic protozoan. In some examples, the viral pathogen is HIV, hepatitis C virus (HCV), Epstein-Barr virus (EBV), human T-lymphotropic virus 1 (HTLV-1), Kaposi's sarcoma herpesvirus (KSHV), equine non-primate hepacivirus (NPHV), or Ebola virus. In some examples, the bacterial pathogen is *Helicobacter pylori, Borrelia burgdorferi* (Lyme disease), *Escherichia coli, Mycobacteria tuberculosis, Staphylococcus aureus, Neisseria gonorrhoeae, Streptococcus pneumoniae, Corynebacterium diphtheria,* or *Vibrio cholera*. In some examples, the fugal pathogen is *Candida albicans*. In some examples, the protozoan parasite is *Plasmodium falciparum, Trypanosoma cruzi, Giardia lamblia, Toxoplasma gondii, Trichomonas vaginalis,* or *Entamoeba histolytica*. In some examples, the helminth is *Strongyloides stercoralis, Onchocerca volvulus, Loa loa,* or *Wuchereria bancrofti*.

Any pathogen listed in section V below or known in the art can be detected using the disclosed methods.

In one nonlimiting embodiment, the method for detecting antigen-specific antibodies in a serum sample comprises providing a fusion protein comprising an antigen fused to a luciferase; contacting a serum sample having a volume of less than 2 μl with the fusion protein, thereby forming immune complexes if antigen-specific antibodies are present in the sample; contacting the immune complexes with magnetic beads coated with protein A/G; isolating the bead-bound immune complexes by directly contacting the bead-bound immune complexes with a neodymium magnet; and detecting emission of light from the isolated bead-bound immune complexes, thereby detecting the presence of antigen-specific antibodies in the biological sample, wherein all steps of the assay are completed in less than five minutes.

Also provided herein is a device for detecting antigen-specific antibodies according to the methods disclosed herein, wherein the device is capable of processing a plurality of samples simultaneously. For example, the device may be used to process multiple samples from a single subject, with each sample being used to detect antibodies specific for a different antigen. Alternatively or in addition, the device may be used to process biological samples from a multitude of different subjects for the detection of a single type of antibody or for the detection of multiple different antigen-specific antibodies. The device includes a first solid support for housing a plurality of biological fluid samples and a second solid support comprising a plurality of neodymium magnets affixed thereto. In some embodiments, the first solid support is a multi-well plate, such as a 6-well plate, a 12-well plate, a 24-well plate, a 48-well plate, a 96-well plate, a 384-well plate or a 1536-well plate. A number of different multi-well plates are commercially available from a variety of sources; a suitable plate can be selected by one of skill in the art. In some embodiments, the second solid support is matched to the first solid support such that the second solid support includes the same number of neodymium magnets as the number of wells present in the multi-well plate, and the neodymium magnets are spaced on the second solid support such that each well is only contacted by a single neodymium magnet.

The length and diameter of the neodymium magnets for the device can be selected based on the corresponding size of the wells of the multi-well plate and volume contained within each well. In some embodiments, the neodymium magnets are about 1 cm to about 5 cm in length, such as about 2 cm to about 4 cm, or about 2.5 cm to about 3.5 cm in length. In some embodiments, the diameter of the neodymium magnet is less than about 1 mm in diameter. In non-limiting examples, the magnet is about 0.9 mm, about 0.8 mm, about 0.7 mm, about 0.6 mm, about 0.5 mm, about 0.4 mm, about 0.3 mm, about 0.2 mm or about 0.1 mm in diameter.

IV. Diagnosis of Autoimmune Disorders

Also provided by the present disclosure are methods of diagnosing a subject as having an autoimmune disease by performing the disclosed methods to detect autoantibodies in a biological sample from the subject that are indicative of the autoimmune disease. In some embodiments, the method includes providing a fusion protein comprising an antigen (such as an autoantigen) fused to a light-emitting protein; contacting a biological fluid sample (from a subject suspected of having an autoimmune disease) with the fusion protein, thereby forming immune complexes if autoantibodies are present in the biological fluid sample; contacting the immune complexes with magnetic beads coated with an immunoglobulin-binding protein to form bead-bound immune complexes; isolating the bead-bound immune complexes by directly contacting the bead-bound immune complexes with a neodymium magnet; and detecting emission of light from the isolated bead-bound immune complexes, thereby diagnosing the subject as having an autoimmune disease.

In some embodiments, the autoimmune diseases is selected from 21-hydroxylase deficiency, acute anterior uveitis, acute disseminated encephalomyelitis (ADEM), acute necrotizing hemorrhagic leukoencephalitis, Addison's disease, gammaglobulinemia, alopecia areata, amyloidosis, ankylosing spondylitis, anti-GBM/Anti-TBM nephritis, antiphospholipid syndrome (APS), autoimmune angioedema, autoimmune aplastic anemia, autoimmune dysautonomia, autoimmune hepatitis, autoimmune hyperlipidemia, autoimmune immunodeficiency, autoimmune inner ear disease (AIED), autoimmune myocarditis, autoimmune oophoritis, autoimmune pancreatitis, autoimmune retinopathy, autoimmune thrombocytopenic purpura (ATP), autoimmune thyroid disease, autoimmune urticarial, axonal and neuronal neuropathies, Balo disease, Behcet's disease, bullous pemphigoid, cardiomyopathy, Castleman disease, celiac disease, Chagas disease, chronic inflammatory demyelinating polyneuropathy (CIDP), chronic recurrent multifocal ostomyelitis (CRMO), Churg-Strauss syndrome, cicatricial pemphigoid/benign mucosal pemphigoid, Crohn's disease, Cogans syndrome, cold agglutinin disease, congenital heart block, coxsackie myocarditis, CREST disease, cryoglobulinemia, demyelinating neuropathies, dermatitis herpetiformis, dermatomyositis, Devic's disease (neuromyelitis optica), discoid lupus, Dressler's syndrome, endometriosis, eosinophilic esophagitis, eosinophilic fasciitis, erythema nodosum, experimental allergic encephalomyelitis, Evans syndrome, fibrosing alveolitis, giant cell arteritis (temporal arteritis), giant cell myocarditis, glomerulonephritis, Goodpasture's syndrome, granulomatosis with polyangiitis (GPA), Graves' disease, Guillain-Barre syndrome, Hashimoto's encephalitis, Hashimoto's thyroiditis, hemolytic anemia, Henoch-Schonlein purpura, herpes gestationis, hypogammaglobulinemia, idiopathic thrombocytopenic purpura (ITP), IgA nephropathy, IgG4-related sclerosing disease, immunoregulatory lipoproteins, inclusion body myositis, inflammatory bowel disease, interstitial cystitis, juvenile arthritis, juvenile diabetes (type 1 diabetes), juvenile myositis, Kawasaki syndrome, Lambert-Eaton syndrome, leukocytoclastic vasculitis, lichen planus, lichen sclerosus, ligneous conjunctivitis, linear IgA disease (LAD), membranous nephropathy, Meniere's disease, microscopic polyangiitis, mixed connective tissue disease (MCTD), Mooren's ulcer, Mucha-Habermann disease, multiple sclerosis, myasthenia gravis, myositis, narcolepsy, neutropenia, ocular cicatricial pemphigoid, optic neuritis, palindromic rheumatism, pediatric autoimmune neuropsychiatric disorders associated with *streptococcus* (PANDAS), paraneoplastic cerebellar degeneration, paroxysmal nocturnal hemoglobinuria (PNH), Parry Romberg syndrome, Parsonnage-Turner syndrome, pars planitis (peripheral uveitis), pemphigus, peripheral neuropathy, perivenous encephalomyelitis, pernicious anemia, POEMS syndrome, polyarteritis nodosa, type I, II, & III autoimmune polyglandular syndromes, polymyalgia rheumatic, polymyositis, postmyocardial infarction syndrome, postpericardiotomy syndrome, progesterone dermatitis, primary biliary cirrhosis, primary sclerosing cholangitis, psoriasis, psoriatic arthritis, pulmonary fibrosis (idiopathic), pyoderma gangrenosum, pure red cell aplasia, Raynauds phenomenon, reactive arthritis, reflex sympathetic dystrophy, Reiter's syndrome, relapsing polychondritis, restless legs syndrome, retroperitoneal fibrosis, rheumatic fever, rheumatoid arthritis, sarcoidosis, Schmidt syndrome, scleritis, scleroderma, Sjögren's syndrome, sperm and testicular autoimmunity, stiff person syndrome, subacute bacterial endocarditis (SBE), Susac's syndrome, sympathetic ophthalmia, systemic lupus erythematosus (SLE), Takayasu's arteritis, temporal arteritis/Giant cell arteritis, thrombocytopenic purpura (TTP), Tolosa-Hunt syndrome, transverse myelitis, type 1 diabetes, ulcerative colitis, undifferentiated connective tissue disease (UCTD), uveitis, vasculitis, vesiculobullous dermatosis, and vitiligo.

In particular non-limiting embodiments, the autoimmune disease is selected from Sjögren's syndrome, type 1 diabetes, rheumatoid arthritis, systemic lupus erythematosus, celiac disease, myasthenia gravis, Hashimoto's thyroiditis and Graves' disease.

In some examples, the autoimmune disease is selected from one of the autoimmune diseases listed in the table below and the method detects autoantibodies against the listed target.

| Disease | Autoantibody Target |
|---|---|
| Acute motor axonal neuropathy (AMAN) | Ganglioside GD3 |
| Antiphospholipid syndrome | Phospholipid |
| APECED | BPIFB1 |
| Celiac disease | tTG |
| Chronic autoimmune hepatitis | Smooth muscle |
| CREST syndrome | Centromere |
| Dermatitis herpetiformis | eTG |

-continued

| Disease | Autoantibody Target |
|---|---|
| dNTM infection | interferon-γ |
| Graves' disease | TSH receptors |
| Hashimoto's thyroiditis | Thyroid peroxidase, thyroglobulin, TSH receptors |
| Immunodysregulation, polyendrocrinopathy, enteropathy X-linked syndrome (IPEX) | Harmonin, villin |
| Inflammatory myopathy | Jo1 |
| Lambert-Eaton myasthenic syndrome | Voltage-gated calcium channel (P/Q type) |
| Limbic encephalitis | Voltage-gated potassium channel (VGKC) |
| Miller-Fisher syndrome | Ganglioside GQ1B |
| Mixed connective tissue disease | Ribonucleoprotein (RNP) |
| Multifocal motor neuropathy with conduction block (MMN) | Ganglioside GM1 |
| Myasthenia gravis | Nicotinic acetylcholine receptor, muscle-specific kinase (MUSK) |
| Neuromyelitis optica (Devic's disease) | Aquaporin-4 (AQP4) |
| Polymyositis | Signal recognition peptide (SRP) |
| Primary biliary cirrhosis | Nucleoporin 62 (p62), sp100 nuclear antigen, nucleoporin 210 kDa, mitochondria |
| Rheumatoid arthritis | IgG, cyclic citrullinated peptide, ADAM33, honerin, HCN3 |
| Sjögren's syndrome | SSA (Ro52 and Ro60), SSB (La) |
| Sporadic inclusion body myositis | Cytosolic 5-nucleosidase 1A (cN1A) |
| Stiff person syndrome | Glutamic decarboxylase-65 (GAD65), amphiphysin, glutamate decarboxylase |
| Systemic lupus erythematosus (SLE) | Sm proteins, U1-RNP-A1, U1-70K RNP, small nuclear RNA (snRNA), dsDNA, histones, thrombin, Ro52, Ro60, La |
| Systemic sclerosis | Topoisomerase, POLR3A |
| Type 1 diabetes | Insulinoma-associated protein-2 (IA2), IA2-β, insulin, GAD65, glutamate decarboxylase, zinc transporter-8 (Znt8) |

In one non-limiting example, the method diagnoses a subject as having Sjögren's syndrome by detecting autoantibodies specific for Ro52, Ro60 and/or La.

V. Diagnosis of Infectious Diseases

The present disclosure also provides methods of diagnosing a subject as infected with a pathogen by performing the disclosed methods to detect pathogen-specific antibodies in a biological sample from the subject. In some embodiments, the method includes providing a fusion protein comprising a pathogen-specific antigen fused to a light-emitting protein; contacting a biological fluid sample (from a subject suspected of having an infectious disease) with the fusion protein, thereby forming immune complexes if pathogen-specific antibodies are present in the biological fluid sample; contacting the immune complexes with magnetic beads coated with an immunoglobulin-binding protein to form bead-bound immune complexes; isolating the bead-bound immune complexes by directly contacting the bead-bound immune complexes with a neodymium magnet; and detecting emission of light from the isolated bead-bound immune complexes, thereby diagnosing the subject as infected with a pathogen.

In some embodiments, the pathogen is a viral pathogen, a bacterial pathogen, a fungal pathogen, a parasitic helminth, or a parasitic protozoan.

Examples of viruses include, but are not limited to those in the following virus families: Retroviridae (for example, human immunodeficiency virus (HIV), human T-cell leukemia viruses; Picornaviridae (for example, poliovirus, hepatitis A virus, enteroviruses, human coxsackie viruses, rhinoviruses, echoviruses, foot-and-mouth disease virus); Caliciviridae (such as strains that cause gastroenteritis, including Norwalk virus); Togaviridae (for example, alphaviruses (including chikungunya virus, equine encephalitis viruses, Simliki Forest virus, Sindbis virus, Ross River virus, rubella viruses); Flaviridae (for example, hepatitis C virus, equine non-primate hepacivirus (NPHV), dengue viruses, yellow fever viruses, West Nile virus, Zika virus, St. Louis encephalitis virus, Japanese encephalitis virus, Powassan virus and other encephalitis viruses); Coronaviridae (for example, coronaviruses, severe acute respiratory syndrome (SARS) virus, Middle East respiratory syndrome (MERS) virus; Rhabdoviridae (for example, vesicular stomatitis viruses, rabies viruses); Filoviridae (for example, Ebola virus, Marburg virus); Paramyxoviridae (for example, parainfluenza viruses, mumps virus, measles virus, respiratory syncytial virus); Orthomyxoviridae (for example, influenza viruses); Bunyaviridae (for example, Hantaan viruses, Sin Nombre virus, Rift Valley fever virus, bunya viruses, phleboviruses and Nairo viruses); Arenaviridae (such as Lassa fever virus and other hemorrhagic fever viruses, Machupo virus, Junin virus); Reoviridae (e.g., reoviruses, orbiviurses, rotaviruses); Birnaviridae; Hepadnaviridae (hepatitis B virus); Parvoviridae (parvoviruses); Papovaviridae (papilloma viruses, polyoma viruses, BK-virus); Adenoviridae (adenoviruses); Herpesviridae (herpes simplex virus (HSV)-1 and HSV-2; cytomegalovirus; Epstein-Barr virus; varicella zoster virus; Kaposi's sarcoma herpesvirus (KSHV); and other herpes viruses, including HSV-6); Poxviridae (variola viruses, vaccinia viruses, pox viruses); and Iridoviridae (such as African swine fever virus); Astroviridae; and unclassified viruses (for example, the etiological agents of spongiform encephalopathies, the agent of delta hepatitis (thought to be a defective satellite of hepatitis B virus). In some examples, the viral pathogen is HIV, HCV, EBV, HTLV-1, KSHV, or Ebola virus.

Examples of bacterial pathogens include, but are not limited to: *Helicobacter pylori, Escherichia coli, Vibrio cholerae, Borelia burgdorferi, Legionella pneumophilia, Mycobacteria* sps (such as. *M. tuberculosis, M. avium, M. intracellulare, M. kansaii, M gordonae), Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (*anaerobic* sps.), *Streptococcus pneumoniae*, pathogenic *Campylobacter* sp., *Enterococcus* sp., *Haemophilus influenzae, Bacillus anthracia, Corynebacterium diphtherias, corynebacterium* sp., *Erysipelothrix rhusiopathiae, Clostridium perfringers, Clostridium tetani, Enterobacter aerogenes, Klebsiella pneumoniae, Pasteurella multocida, Bacteroides* sp., *Fusobacterium nucleatum, Streptobacillus moniliformis, Treponema pallidium, Treponema pertenue, Leptospira, Bordetella pertussis, Shigella flexnerii, Shigella dysenteriae* and *Actinomyces israelli*.

Examples of fungal pathogens include, but are not limited to: *Cryptococcus neoformans, Histoplasma capsulatum, Coccidioides immitis, Blastomyces dermatitidis, Chlamydia trachomatis* and *Candida albicans*.

Other pathogens (such as parasitic pathogens) include, but are not limited to: *Plasmodium falciparum, Plasmodium vivax, Trypanosoma cruzi* and *Toxoplasma gondii*. (*Plasmodium* species), amoebiasis (*Entamoeba* species), giardiasis (*Giardia lamblia*), toxoplasmosis (*Toxoplasma gondii*), cryptosporidiosis (*Cryptosporidium* species), trichomoniasis (*Trichomonas vaginalis*), Chagas disease (*Trypanosoma cruzi*), Leishmaniasis (*Leishmania* species), sleeping sickness (*Trypanosoma brucei*), amoebic dysentery (*Entamoeba histolytica*), acanthamoeba eeratitis (*Acanthamoeba* species), and primary amoebic meningoencephalitis (*Naegleria fowleri*)

Examples of helminth pathogens include *Strongyloides stercoralis* (causes strongyloidiasis); *Onchocerca volvulus* (causes river blindness/Robles disease); *Loa loa* (filarial nematode that causes *Loa loa* filariasis); and *Wuchereria bancrofti* (roundworm that causes lymphatic filariasis).

In one non-limiting example, the method diagnoses a subject as having HIV by detecting antibodies specific for reverse transcriptase.

VI. Luciferase Immunoprecipitation Systems (LIPS)

LIPS has been previously described in, for example, Burbelo et al., *J Vis Exp* 32:1549, 2009; Burbelo et al., *Expert Rev Proteomics* 8(3): 309-316, 2011; Burbelo and O'Hanlon, *Curr Opin Rheumatol* 26:717-723, 2014; and Burbelo et al., *Transl Res* 165(2):325-335, 2015. LIPS is a fluid-phase immunoassay that employs light-emitting tagged antigens (e.g., *Renilla* luciferase (Ruc)-tagged antigens) to detect antibodies specific for target antigens, such as autoantigens or pathogen-specific antigens. Chimeric nucleic acid molecules encoding antigens fused to a light-emitting protein, such as *Renilla* luciferase, are expressed in mammalian cells, and crude extracts are prepared and used in immunoprecipitations assays to yield quantitative antibody profiles. LIPS has been shown to be capable of detecting both linear and conform-specific epitopes.

In many cases, the gene encoding the 30-kDa *Renilla* luciferase (from the soft coral *Renilla reniformis*) is used as the reporter in LIPS because it has a highly linear output spanning over seven orders of magnitude. Mammalian expression vectors encoding Ruc-antigen fusions are constructed using standard molecular biological techniques. For example, the pREN2 vector can be used to fuse antigens in frame with Ruc. Any one of a number of protein antigen targets can be used with this system, including full-length proteins, protein variants, protein fragments and short peptides.

To perform LIPS, plasmids encoding light-emitting antigen fusions are transfected into mammalian cells, such as Cos 1 cells. Since the antigen is directly tagged with the light-emitting protein, crude extracts can be used without the need for protein purification following expression. Crude extracts of the light-emitting protein-antigen fusions can be stored frozen for later use. Defined amounts (based on light units) of the light-emitting protein-antigen fusion is incubated with the serum sample. If antigen-specific antibodies are present in the serum, they bind to the fusion protein. The reaction mixture is then transferred to a filter plate containing antibody capturing reagents, such as Protein A/G beads or secondary immunoglbulin-immobilized beads. Unbound luciferase-tagged antigen is removed from the microtiter filter plate by multiple washing steps. The relative amount of antibody bound to the luciferase-tagged antigen can be determined by measuring the light produced in the presence of luciferase substrate.

Although LIPS alone is more rapid than performing a standard ELISA or Western blot, the assayusually takes about 2.5 hours and requires extensive washing steps usually on a vaccum manifold. However, the methods disclosed herein, which combine LIPS with a neodymium magnet, greatly improve the speed of the assay such that antigen-specific antibodies can be detected, with high specificity and sensitivity, within one minute. The neodymium magnet is capable of rapidly and efficiently collecting suspended paramagnetic beads bound to immune complexes. Furthermore, there is very low background binding to the neodymium magnetic sticks.

The following examples are provided to illustrate certain particular features and/or embodiments. These examples should not be construed to limit the disclosure to the particular features or embodiments described.

EXAMPLES

Example 1: Rapid Antibody Detection for the Diagnosis of Autoimmune and Infectious Diseases Disclosed herein is the development of "LIPSTICK" for measuring antibodies by employing magnetic sticks in immunoprecipitation (FIG. 1). In this method, cell extracts of luciferase-antigen fusions and sera are incubated together, which is then followed by the addition of paramagnetic protein A/G beads. Next axially, magnetized neodymium magnets (2"×0.75") are used to capture protein A/G-antibody-antigen complexes. The magnets are washed twice in buffer and the antigen-specific antibody is quantified by placing the magnet in a tube of coelenterazine and the luciferase activity is measured in a tube luminometer. In addition to the single, simple washing step for LIPSTICK, one major difference compared to the previous LIPS formats is the deployment of paramagnetic protein A/G beads, which have a much lower IgG-binding capacity (0.5 µg IgG/ml) than the previously employed ULTRALINK™ protein A/G beads (vs. 25 µg/ml). However, unlike the protein A/G ULTRALINK™ beads which settle out quickly during the incubation period, the paramagnetic protein A/G beads remain in suspension (FIG. 1).

Results

Detection of autoantibodies against three different autoantigens, Ro52, Ro60 and La) is useful for the diagnosis of the autoimmune disease, Sjögren's syndrome (SS) (Burbelo et al., *Autoimmunity* 42(6):515-524, 2009). To examine the characteristics of the LIPSTICK assay, a previously described *Renilla* luciferase (Ruc)-Ro52 fusion protein (Burbelo et al., *Am J Transl Res* 2(2):145-155, 2010) was utilized with representative serum samples from a seronegative, control subject and a seropositive patient with Sjögren's syndrome (SS). The assay conditions for initial testing consisted of 0.1 µl of sera, 200 million light units (LU) of Ruc-Ro52 as input, which were tested by a short 25 second incubation step for formation of the antigen-antibody complex, followed by adding the paramagnetic protein A/G beads for 25 seconds, and then a single wash and LU read (10 seconds). As shown in FIG. 2A, this one minute assay demonstrated that increasing the amount of paramagnetic protein A/G beads over a range of 2-20 µl yielded LU that were proportional to the amount of paramagnetic protein A/G beads employed. Over the different protein A/G concentrations, there were over 20 times more light units with the SS sample than the control samples.

Figure 2B:
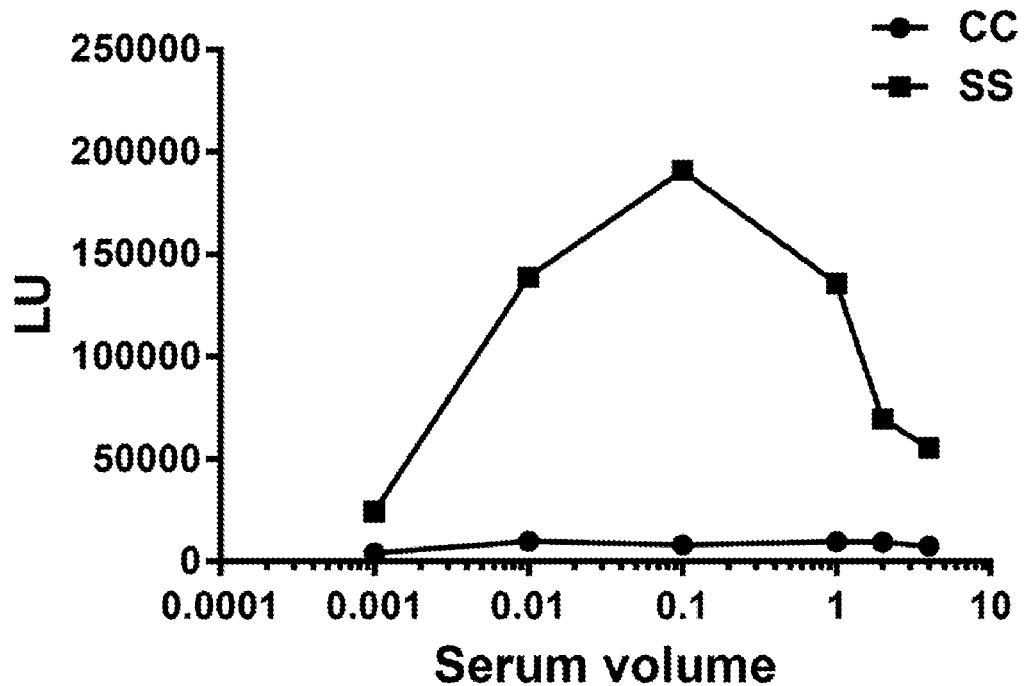
Figure 2C:
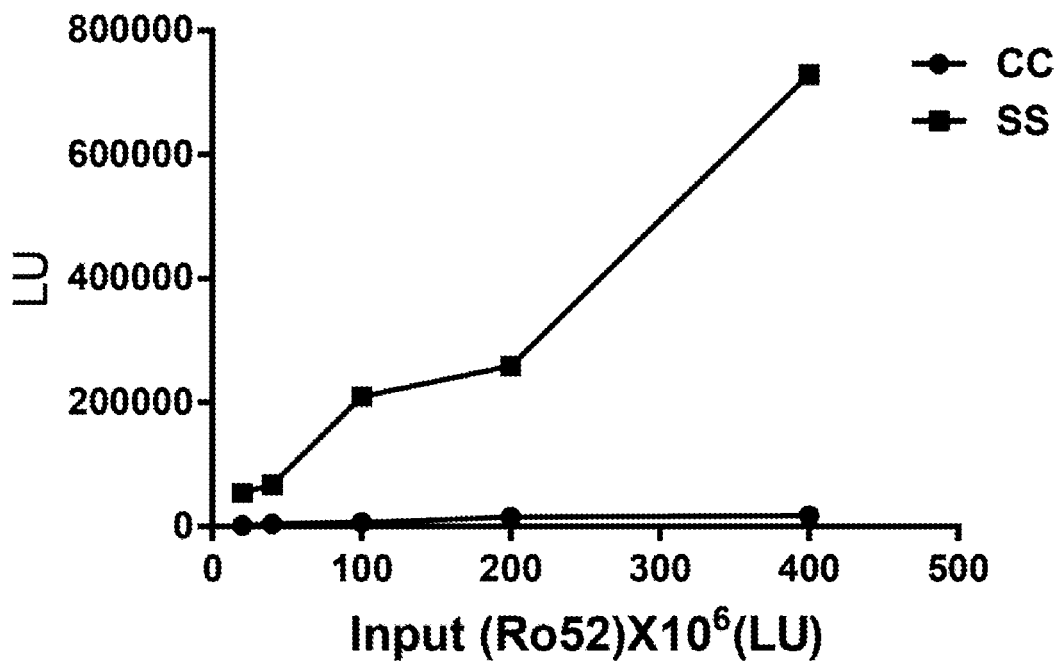

Using 10 µl of the Ruc-Ro52 extract as input, but varying the amount of serum from 0.001 µl to 4 µl in the one minute assay, demonstrated that the highest signal was obtained with 0.1 µl of serum (FIG. 2B), which likely reflected the maximum amount of immunoglobulin captured by this volume of paramagnetic beads. The LU signal in the seropositive SS sample also increased roughly linearly with the addition of increasing amounts of the Ruc-Ro52 extract (FIG. 2C).

Figure 2D:
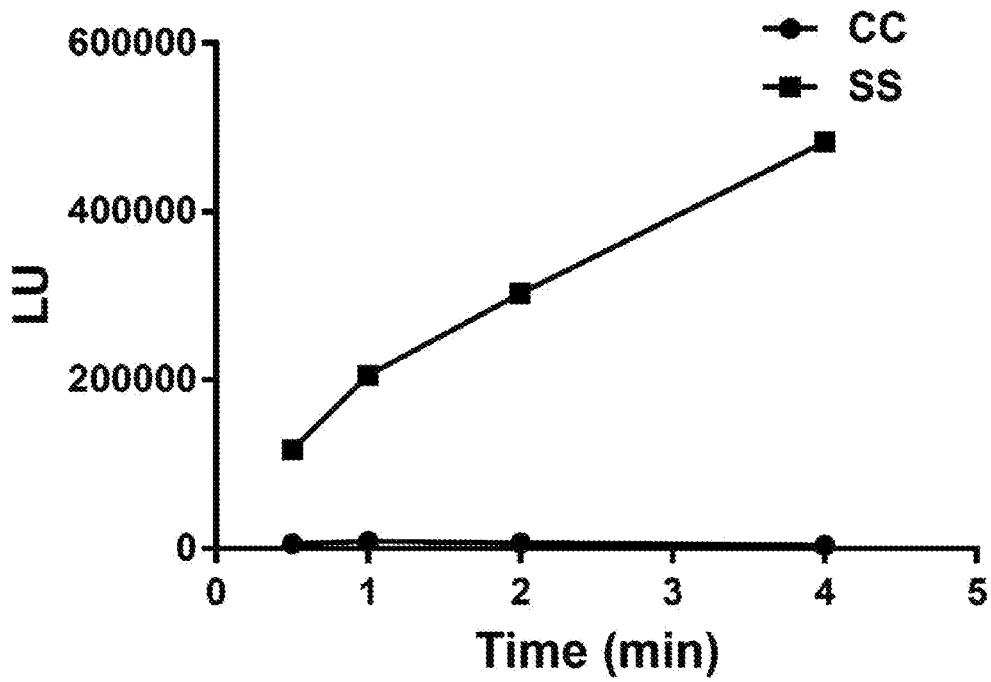

Lastly, extending the assay time from 30 seconds to 4 minutes produced a 5-fold increase in the signal to noise ratio, yielding an overall difference between the seronegative and seropositive samples of 50-fold (FIG. 2D). Additional experiments revealed that the formation of the antibody-antigen complex during the first incubation step was rate-limiting and that the second incubation step involving binding of the immunoglobulin-complex to the paramagnetic beads occurred essentially instantaneously. Overall, these experiments highlight the linearity and robustness of the signal obtained over a wide range of LIPSTICK conditions and suggests that only a single, rapid and simple wash step of the neodymium magnetic sticks is sufficient to produce useful serological data.

Figure 3B:
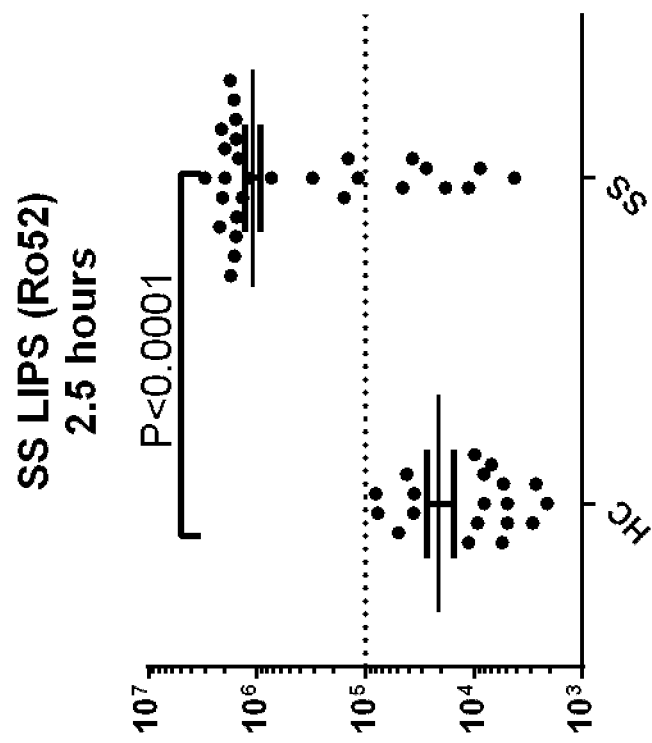
FIGS. 3A-3B are a pair of graphs showing detection of Ro52 autoantibodies. A sample set of 20 healthy controls (HC) and 28 Sjögren's syndrome (SS) patients was examined for Ro52 autoantibodies. Each dot represents the value for each individual.
Figure 3A:
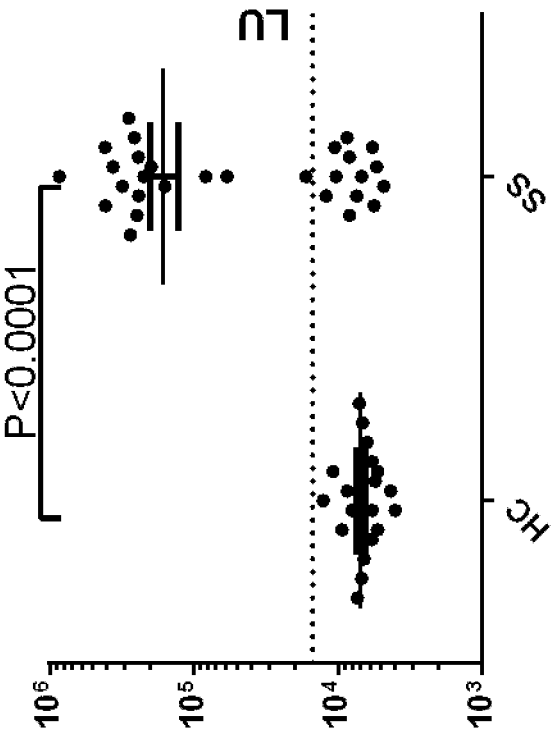

Based on a one-minute LIPSTICK format (0.1 µl of sera, 200 million Ro52 input and 10 µl of paramagnetic protein A/G beads), a cohort of control (n=20) and SS (n=28) serum samples were evaluated and the results were compared with the standard 2.5 hour LIPS format. For all further mention of diagnostic performance, the mean plus three standard deviations of the controls was used to calculate sensitivity and specificity. As shown in FIG. 3, LIPSTICK demonstrated a dynamic range of 4,330 to 856,347 LU within the cohort of controls and SS samples. Evaluation of the sensitivity and specificity of a LIPSTICKS test for detecting SS revealed 54% sensitivity ($^{15}/_{28}$) and 100% specificity and produced results with a lower sensitivity (75% sensitivity and 100% specificity) than the 2.5 hour LIPS test. Several of the SS samples detected in the standard LIPS assay were not detected by LIPSTICKS, which were likely due to the presence of low affinity and/or low titer antibodies in these samples.

Figure 4A:
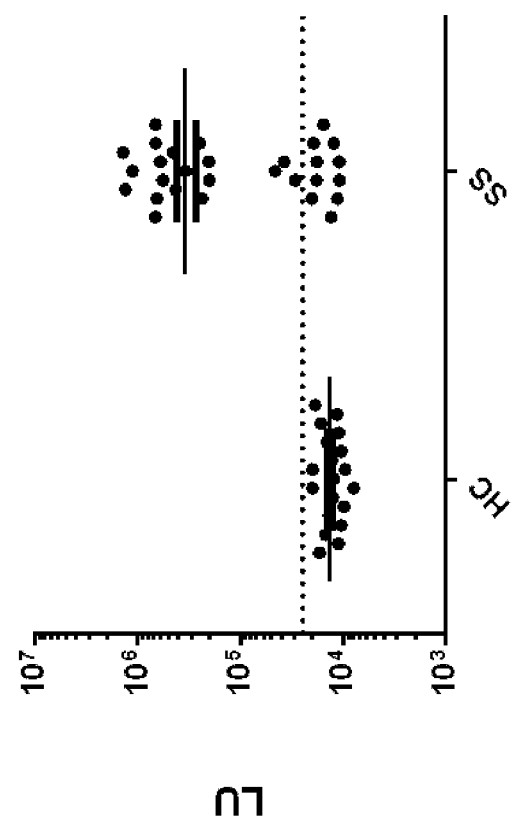
FIGS. 4A-4B are a pair of graphs showing detection of Ro60 and Ro52 autoantibodies. A sample set of 20 HC and 28 SS patients was examined by LIPSTICKS for (FIG. 4A) Ro60 autoantibodies or (FIG. 4B) both Ro60 and Ro52 autoantibodies as a mixture. The cut-off values used to determine diagnostic performance are indicated with the dotted line. The mixture assay showed improved sensitivity compared to either Ro60 or Ro52 alone by LIPSTICK testing.
Figure 4B:
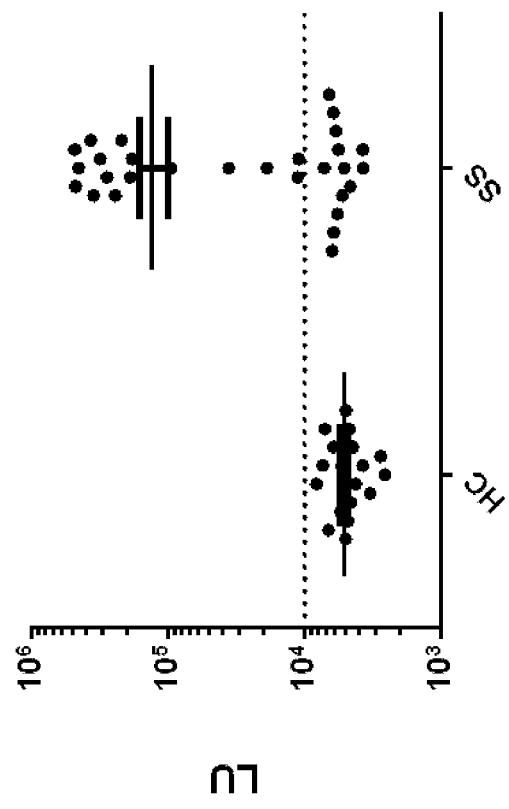

To determine the performance of another autoantigen in the LIPSTICKS format for the diagnosis of SS, the Ro60 autoantigen was tested (Ching et al., *PLoS ONE* 7(2): e32001, 2012). The input for the Ruc-Ro60 LIPSTICK test was 200 million. The Ro60 LIPSTICK test demonstrated 57% sensitivity ($^{16}/_{28}$) and 100% specificity and produced diagnostic results again slightly lower than the 2.5 hour Ro60 LIPS test (FIG. 4A). Based on the ability of combining antigens in LIPS (Burbelo et al., *Transl Res* 165(2):325-335, 2015; Burbelo et al., *PLoS Negl Trop Dis* 3(5):e438, 2009; Burbelo et al., *Clin Vaccine Imunol* 16(5):621-627, 2009), a mixture of Ro52 and Ro60 (200 million of each extract) was used in LIPSTICK in the one minute assay. As shown in FIG. 4B, there was an additive response employing Ro52 and Ro60 together as a mixture in LIPSTICK testing, which showed improved sensitivity of 64% sensitivity and 100% specificity than using either by itself. These results with the one minute LIPSTICK test are also as good as a clinical ELISA that takes 3-4 hours to perform. These findings highlight how mixtures of antigens can be analyzed simultaneously in LIPSTICK to improve diagnostic performance.

A third autoantigen, La/SSB (Burbelo et al., *Autoimmunity* 42(6):515-524, 2009), was also evaluated with the cohort. The input for each assay was approximately 250 million. In contrast to Ro52 and Ro60 LIPSTICK testing, only a few of the samples were seropositive for La compared to the standard assay (compare FIG. 5A and FIG. 5C). To determine if longer incubation might improve the detection of the SS samples containing low affinity and/or low titer autoantibodies, the assay was extended to 59 minutes and protein A/G beads were added for only one minute and processed. As shown in FIG. 5B, lengthening the time improved the signal and sensitivity. The one minute La LIPSTICK test yielded 25% sensitivity ($^{7}/_{28}$), the one hour La LIPSTICK test yielded 53% sensitivity ($^{15}/_{28}$) and the standard 2.5 hour LIPS test yielded 61% sensitivity ($^{17}/_{28}$). The clinical ELISA test only has 45% sensitivity.

Figure 6:
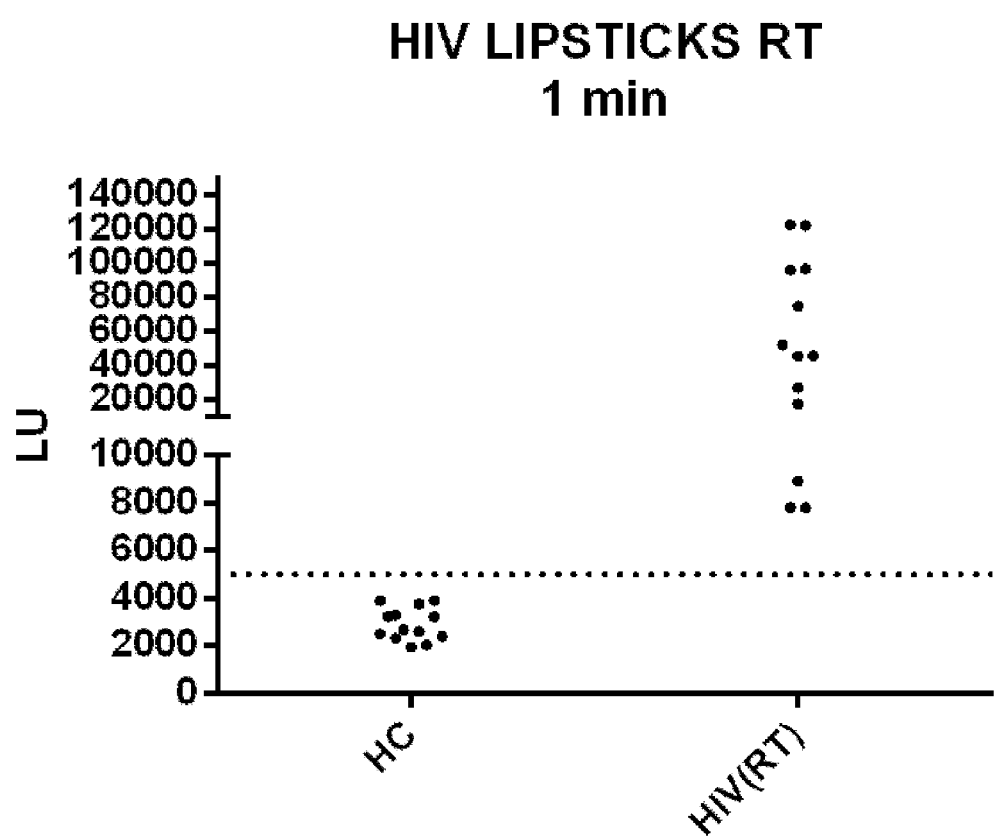
FIG. 6 is a graph showing detection of human immunodeficiency virus (HIV) reverse transcriptase (RT) antibodies. A sample set of 13 healthy uninfected controls (HC) and 13 HIV patients was examined for antibodies against HIV RT for the diagnosis of HIV. Compared to the other LIPSTICK assays for Ro52, Ro60 and La autoantibodies, approximately one tenth the input (20 million total) of Ruc-HIV RT was used. The cut-off values used to determine diagnostic performance are indicated with the dotted line. The one minute LIPSTICK RT test showed 100% sensitivity and 100% specificity.

To determine the effectiveness of LIPSTICKS for the diagnosis of an infectious agents, a Ruc-HIV reverse transcriptase antigen (Burbelo et al., *J Infect Dis* 209(10):1613-1617, 2014; Burbelo et al., *Biochem Biophys Res Commun* 352(4):889-895, 2007) was evaluated for HIV testing in the one minute rapid LIPSTICK format. In this assay, only 20 million of total input LU was added per sample. As shown in FIG. 6, using only 20 million LU of input showed a low background in all the healthy uninfected controls. However, seropositive signals were detected in all 13 HIV samples. These g results represent the fastest diagnostic test for HIV that has ever been developed.

Diagnostic Applications

Described herein is a simple and rapid immunoassay format based on performing an immunoprecipitation reaction in solution and capturing the immune complexes on the end of a magnet. It is believed that LIPSTICKS can be used to obtain a diagnostic result in less than five minutes for any one of a number of infectious and autoimmune diseases. One of the key features of the assay is the magnets that show low background binding. Although magnets have been used previously used in various scientific applications, a key feature of LIPSTICKS is to directly use the magnet in the reaction and not on the outside of the vessel. For manual testing, the magnets are recyclable and can be used over and over again. The magnets can also be used with hand-held luminometers (which are commercially available) to further enable the assay for POCT. The use of the magnetic sticks provides a simple format for processing the reaction and eliminates extensive washing and liquid handling steps that are needed in other immunoprecipitation formats. In addition to the simple wash step needed for LIPSTICK, one major difference compared to the previous LIPS format is the deployment of paramagnetic protein A/G beads, which have a much lower IgG-binding capacity (0.5 µg IgG/ml) than the previously employed ULTRALINK™ protein A/G beads (vs. 25 µg/ml). However, unlike the protein A/G ULTRALINK™ beads which settle out quickly during the incubation period, the paramagnetic protein A/G beads remain in suspension (FIG. 1).

Example 2: Ultrarapid Measurement of Diagnostic Antibodies by Magnetic Capture of Immune Complexes Rapid and inexpensive antibody quantitation is needed for clinical diagnostics. This example describes LIPSTICKS, a simple and robust fluid-phase immunocapture method utilizing neodymium magnetic sticks to capture protein A/G coated paramagnetic beads bound to antibody/luciferase-labeled antigen complexes. The data in this example demonstrates that this system effectively measures specific antibody levels in serum samples from subjects with a variety of different infectious or autoimmune disorders. In the case of Sjögren's syndrome, antibody levels are measured directly from saliva, requiring only about one minute per assay.

Background

There is great interest in developing point-of-care (POC) clinical immunoassays to detect antibodies for the rapid diagnosis of infectious and autoimmune diseases. Solid-phase POC formats such as lateral flow immunoassays and miniaturized ELISAs show great promise, however, the number of available tests are few and they require 10 minutes to several hours for completion, often not yielding quantitative results (Chin et al., *Nat Med* 17(8):1015-1019, 2011; Laksanasopin et al., *Sci Transl Med* 7(273):273 rel, 2015).

Fluid-phase immunoprecipitation assays efficiently detect linear and conformational epitopes and typically show the highest sensitivity for assessing the presence and the level of serum antibodies in various autoimmune and infectious diseases (Liu and Eisenbarth, *Clin Immunol* 125(2):120-126, 2007; Burbelo P et al., *Transl Res* 165(2):325-335, 2015). One fluid-phase immunoassay technology, the Luciferase Immunoprecipitation Systems (LIPS), utilizes light-emitting luciferase-antigen fusion proteins added to the sample and recaptured in the presence of specific antibody reacting with it to detect antibodies in clinical samples (Burbelo P et al., *Transl Res* 165(2):325-335, 2015). LIPS has demonstrated high sensitivity and specificity in the detection of antibodies in many different infectious and autoimmune diseases (Burbelo P et al., *Transl Res* 165(2):325-335, 2015). LIPS has several advantages over other methods, including a high signal-to-noise ratio, modular format and the ability to multiplex. Described herein is an alternative high-speed, streamlined modification of the LIPS assay, termed LIPSTICKS.

Methods

Serum and Saliva Samples

Control and patient serum and/or saliva samples were obtained from human subjects. Five cohorts of human samples along with corresponding controls were used: HIV-infected subjects, Epstein-Barr Virus (EBV)-infected, disseminated non-tuberculosis mycobacterial (dNTM) infection, autoimmune polyendocrinopathy-candidiasis-ectodermal dystrophy (APECED) and Sjögren's syndrome (SS) samples. Additional samples for animal health monitoring included uninfected and HNPV-infected serum samples from horses.

HIV cohort: Serum samples from HIV uninfected (n=24) and HIV-infected subjects (n=25) were used. The samples from untreated HIV-infected subjects had a median viral load of 29,494 copies/ml (interquartile range of 8,814-79, 989). Additional testing from eight HIV-infected subjects from before and after long term anti-retroviral treated were also used and have been previously described (Burbelo et al., *J Infect Dis* 209(10):1613-1617, 2014).

EBV cohort: Human samples were serologically evaluated for EBV infection with an EBV viral capsid antigen (VCA) ELISA (Trinity Biotech). However, following LIPSTICKS analysis, two samples detected as positive by LIPSTICKS but negative by ELISA were further studied in detail and were confirmed to be seropositive for two additional EBV antigens (p18 and p24) consistent with published studies. In total, 39 samples (15 EBV uninfected and 24 EBV-infected sera) were studied.

dNTM: Disease controls and subjects having dNTM with interferon-γ autoantibodies have been previously described (Browne et al., *N Engl J Med* 367(8):725-734, 2012). For LIPSTICKS, a random set of controls (n=17) and dNTM patients (n=13) was studied and compared to previous testing.

APECED: Serum samples from healthy controls (n=17) and APECED subjects (n=23) were used. Since no available ELISA data was available for BPIFB1 autoantibodies, the 2.5 hour LIPS assay with a BPIFB1-*Gaussia* luciferase detector was used to assess seropositivity.

Sjögren's syndrome: Healthy controls and SS patients were studied, in which the diagnosis of SS fulfilled the revised European consensus criteria (Vitali et al., *Ann Rheum Dis* 61(6):554-558, 2002). Autoantibodies against SSA and SSB were determined by ELISA. Saliva samples obtained from the parotid gland were obtained from SS (n=17) and healthy volunteers (n=18). Another set of serum samples from SS (n=29) and healthy volunteers (n=19) were also studied.

Equine nonprimate hepacivirus virus (NPHV) infection: A cohort of horses with and without NPHV infection has been previously described (Burbelo et al., *J Virol* 86(11): 6171-6178, 2012). A subset of horse samples with (n=4) and without (n=7) NPHV infection were used in LIPSTICKS.

Plasmids and Recombinant Antigens

Table 1 provides details about the ten different luciferase antigen fusion constructs used in this study. Mammalian expression plasmids expressing *Renilla* luciferase light-emitting antigen fusions for HIV p24 (Burbelo et al., *J Infect Dis* 209(10):1613-1617, 2014), HIV reverse transcriptase (Burbelo et al., *J Infect Dis* 209(10):1613-1617, 2014), EBV EBNA1 (Bu et al., *Clin Vaccine Immunol* 23(4):363-369, 2016), NHPV helicase (Burbelo et al., *J Virol* 86(11):6171-6178, 2012), human Interferon-γ (Browne et al., *N Engl J Med* 367(8):725-734, 2012), human Ro52 (Burbelo et al., *Autoimmunity* 42(6):515-24, 2009), human Ro60 (Ching et al., *J Dent Res* 90(4):445-449, 2011) and human La (Burbelo et al., *Autoimmunity* 42(6):515-24, 2009), have been previously described. Two new mammalian vectors expressing *Gaussia* and NANOLUC™ luciferases for BPIFB1 and Ro52, respectively, were also generated.

TABLE 1

Description of Luciferase-Antigen Fusions

| Plasmid | Disease/Infection | Antigen | Luciferase | Type of Antigen Fusion |
|---|---|---|---|---|
| PREN-p24 | HIV | P24 HIV capsid | *Renilla* Luciferase | C-terminal |
| pREN2-RT | HIV | P24 HIV reverse transcriptase | *Renilla* Luciferase | C-terminal |
| pREN2-EBNA1 | EBV | EBNA1 | *Renilla* Luciferase | C-terminal |
| pREN2-CHV | NHPV | Helicase | *Renilla* Luciferase | C-terminal |
| pREN2-IFN-γ | dNTM | Interferon-γ | *Renilla* Luciferase | C-terminal |
| pGaus3-BPIFB1 | APECED | BPIFB1 | *Gaussia* Luciferase | N-terminal |
| pREN2-Ro52 | SS | Ro52 | *Renilla* Luciferase | C-terminal |
| pREN2-Ro60 | SS | Ro60 | *Renilla* Luciferase | C-terminal |
| pREN2-La | SS | La | *Renilla* Luciferase | C-terminal |
| pNano-Ro52 | SS | Ro52 | NANOLUC ™ | N-terminal |

To prepare recombinant light emitting proteins, Cos-1 cells were grown in DMEM supplemented with 10% FBS, 1% glutamine and penicillin-streptomycin. Cells were seeded in 100 mm dishes the day before transfection. Transfections (2 µg) were performed with Fugene-6 (Promega) per the manufacturer's instructions. Forty-eight hours after transfection, the plates were washed once with PBS, scraped in 0.2 ml Buffer A (20 mM Tris, pH 7.5, 150 mM NaCl, 5 mM $MgCl_2$, 1% Triton X-100), the cells were collected and centrifuged twice at 13,000×g for 4 minutes, then the supernatants were collected and used immediately. Alternatively, the extracts are harvested in Buffer A containing protease inhibitors and 50% glycerol and then stored frozen at −80° C. Total luciferase activity in 1 µl of each crude extract was measured by adding it directly to 100 µl of assay buffer and substrate mixture (*Renilla* Luciferase Reagent Kit, Promega) in a clear 1.5 ml microfuge tube, vortexing and immediately measuring in a luminometer (Turner design 20/20, Promega) for 1 second.

Magnets and Paramagnetic Beads

Two sizes of neodymium magnetic cylinders ("sticks"; K&G Magnets) were initially tested: 1.59 mm diameter× 25.4 mm thick (Cat # D2X0; 1/8" diameter×1" thick) and 1/16" diameter×25.4 mm thick (Cat # D1X0; 1/16" diameter×1" thick). The 1/16" magnets produced a better detectable light signal, which was likely due to less physical quench of the light. To simplify handling of the magnets during the assay, two different size magnets were combined, whereby the 1/16" diameter magnet was stuck together with the 1/8 diameter such that 1/16" diameter magnet side was utilized to capture the paramagnetic beads. Following the assay, the neodymium magnets were reused after decontamination and stripping of the bound beads. This was easily accomplished by first placing in 0.1% bleach disinfectant, physically removing the paramagnetic beads from the magnets with a paper towel, and then rinsing the cleaned magnets with water.

Three different sizes of paramagnetic protein A/G-coated beads were tested including 1-2.5 diameter (Product #88803; Thermo Scientific/Pierce protein A/G magnetic beads), 1µ diameter Hi—Sur Mag Protein A/G (Ocean Nanotech), and 500 nm diameter Supermag protein A/G beads (Ocean Nanotech). The two smaller beads of 1µ and 500 nm diameters needed more time, approximately 15 and 45 seconds, respectively, to be captured by the magnets from the 100 µL reaction volumes. Thus, the Thermo Scientific/Pierce protein A/G magnetic beads were used in LIPSTICKS. Additional experiments titrating these beads revealed that 5 µL of beads (diluted 1:5 in water from the stock) provided an adequate signal to noise output for the LIPSTICKS assay.

LIPSTICKS Tube Assay

The LIPSTICKS tube assay involves several steps and can be performed in approximately 45 seconds, in part due to the tube luminometer requiring only a 1 second integration time to read the sample (FIG. 1). To initiate the assay, 5 µl of the diluted serum sample (1:10 in buffer A) or 10 µl of undiluted saliva was added to 5 µl of the luciferase-tagged antigen in a 1.5 ml microfuge tube. For the different antigen fusions used in the assays, the total input activity was approximately 50-100 million LU/µl. Next, 100 µl buffer A was added and the reaction mixture was immediately vortexed for 2 seconds. Then, 5 µl diluted paramagnetic beads (1:5 in water) was pipetted into the reaction mix and the tube was tapped two times to evenly disperse the beads. The magnetic stick was then immersed into the tube containing the beads for 5 seconds. The magnet was removed and dipped twice in wash buffer. Lastly, the magnetic stick was placed in a tube, preloaded in the luminometer (Turner design 20/20) containing 100 µl coelenterazine substrate, and then read for an integration time of 1 second.

Handheld LIPSTICKS

The hand-held, battery operated, portable, EnSURE luminometer (Hygiena) was also employed for testing. In order to measure luciferase activity from the beads bound to the magnet, the Ultrasnap cap tubes supplied by the manufacturer (Hygiena) were first emptied of their contents and then rinsed three times with distilled water. For LIPSTICKS testing, the cleaned, empty tubes were refilled with 100 µl Nanoglow substrate (Promega). The magnet was then simply dropped into the Ultrasnap tube, recapped and placed in the EnSURE luminometer. An integration time of 15 seconds was used to read the light emitted by the antigen/antibody complex. Unlike *Renilla* luciferase antigen fusions, the Ro52-NANOLUC™ produced a high output with a stable glow with its substrate and is highly detectable during the long integration time with the handheld luminometer. Due to additional integration time of 15 seconds, these tests required 1 minute for completion. For additional comparison, LIPSTICK testing of the Ro52-NANOLUC™ was also performed with the tube luminometer.

Results

LIPSTICKS is based on the magnetic capture of luciferase-tagged immune complexes for the ultrafast measurement of antibodies in clinical samples (FIG. 1). In LIPSTICKS, extracts from cells producing recombinant luciferase-antigen fusion proteins are incubated with serum or saliva samples in a microfuge tube, followed by the addition of buffer and then paramagnetic protein A/G-coated beads. A unique feature of the assay is the use of axially neodymium magnetized sticks that are placed directly into the reaction mixture, capturing in seconds the immune complexes. Non-specifically associated labeled antigen is removed by simply dipping the sticks in wash buffer. The antigen-specific antibody is measured by placing the sticks into tubes containing coelenterazine substrate preloaded in a luminometer and the luciferase activity present is quantified in light units (LU).

It was found that the detection of antibodies by LIPTICKS was affected by several parameters. With the aid of a tube luminometer, the assay was optimized using a *Renilla* luciferase-HIV p24 antigen fusion protein (Burbelo et al., *J Infect Dis* 209(10):1613-1617, 2014) and serum samples from HIV-infected and uninfected subjects. It was determined that 1.59 mm diameter neodymium magnetic sticks bound with beads produced a larger LU signal than 3.18 mm diameter sticks because they quenched less luciferase-generated light. Additional comparisons of various bead diameters revealed similar immunoglobulin-binding capacities, but the 1 µm diameter protein A/G beads were chosen because they required only a short time (<5 sec) to be captured (Table 1).

Figure 7A:
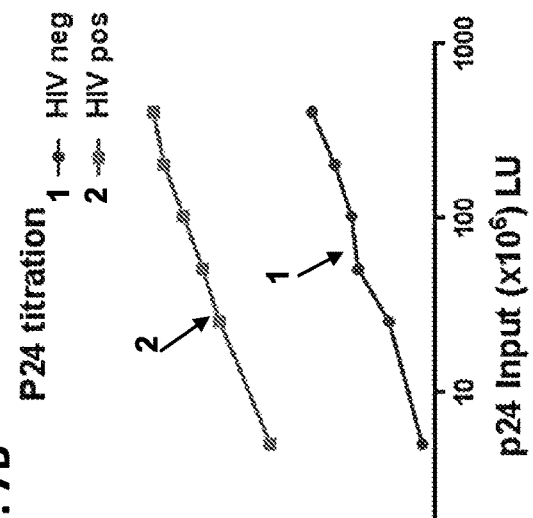
FIGS. 7A-7D are graphs that provide an overview of the LIPSTICKS diagnostic performance.
Figure 7B:
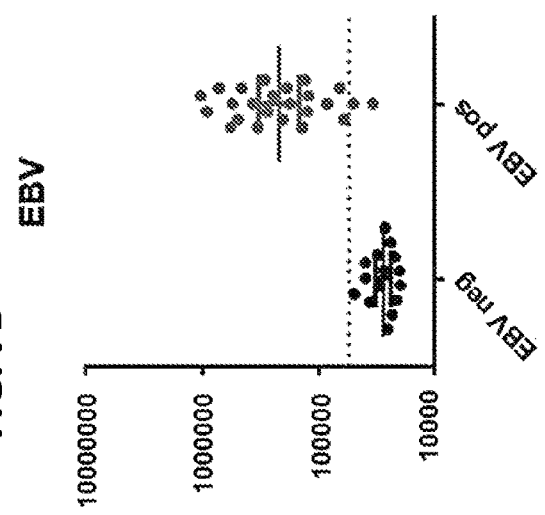
Figure 9B:
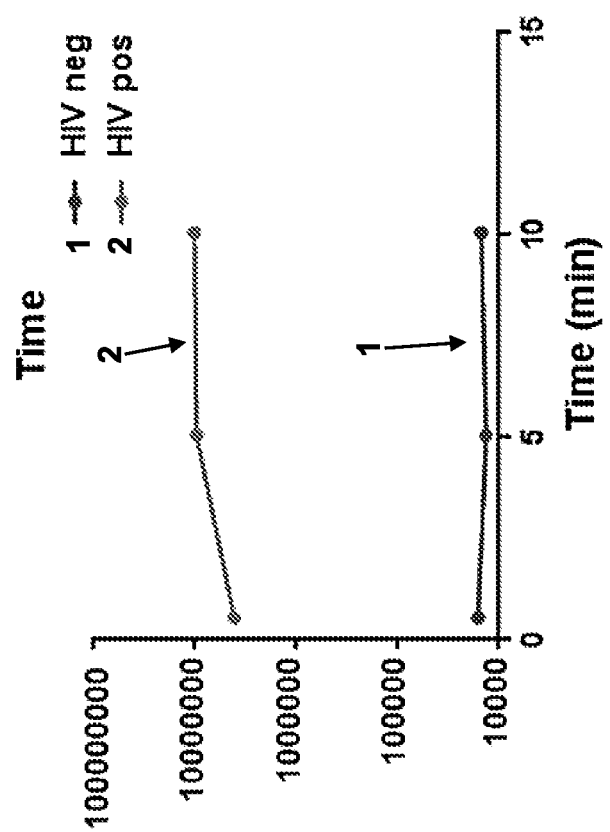
FIGS. 9A-9B are a pair of graphs showing evaluation of additional parameters for LIPSTICKS testing.
Figure 9A:
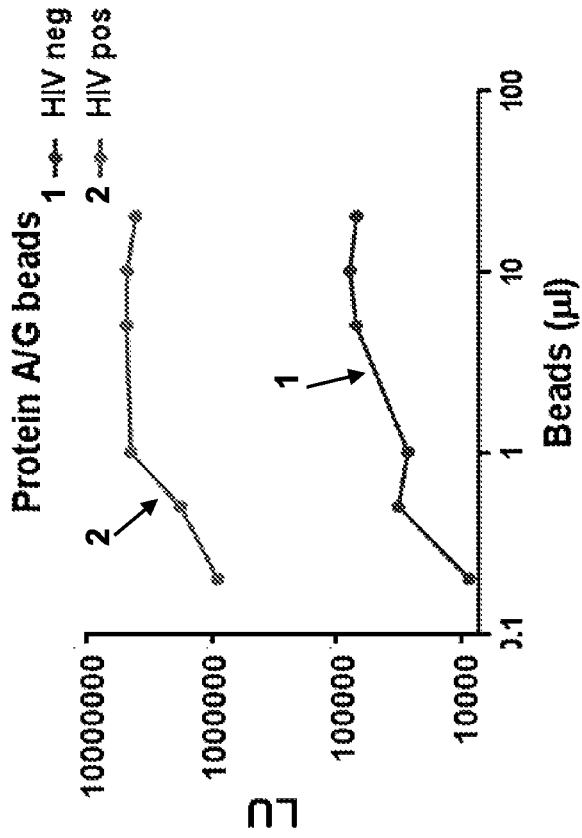

Varying the amount of serum from 0.001 to 4 µL in the one minute assay produced 24-200 times more LU from the HIV-positive compared to the uninfected sample (FIG. 7A). The highest signal-to-noise ratio for detecting antibodies was obtained with 0.1 µL serum, yielding 21,740 LU for the HIV-negative sample vs. 4,545,000 LU for the HIV-positive sample yielding acceptable positive and negative signals given their magnitude. Using more than 0.1 µL of serum decreased the signal due to uncomplexed immunoglobulins competing and displacing the binding of the luciferase-tagged antigen-antibody complexes to the protein A/G beads. The addition of larger amounts of the luciferase-p24 extract demonstrated a roughly parallel increase in the light signal in both the seronegative and seropositive samples (FIG. 7B). Similarly, varying the amount of beads over a range of 0.1 to 5 µL also yielded linearity in the LU signal in both the negative and positive samples, but 1 µL beads yielded a sufficiently high signal-to-noise ratio (FIG. 9A). Lastly, extending the incubation time from one minute to five minutes generally produced a 2-fold increase in the signal-to-noise ratio (FIG. 9B).

Figure 7C:
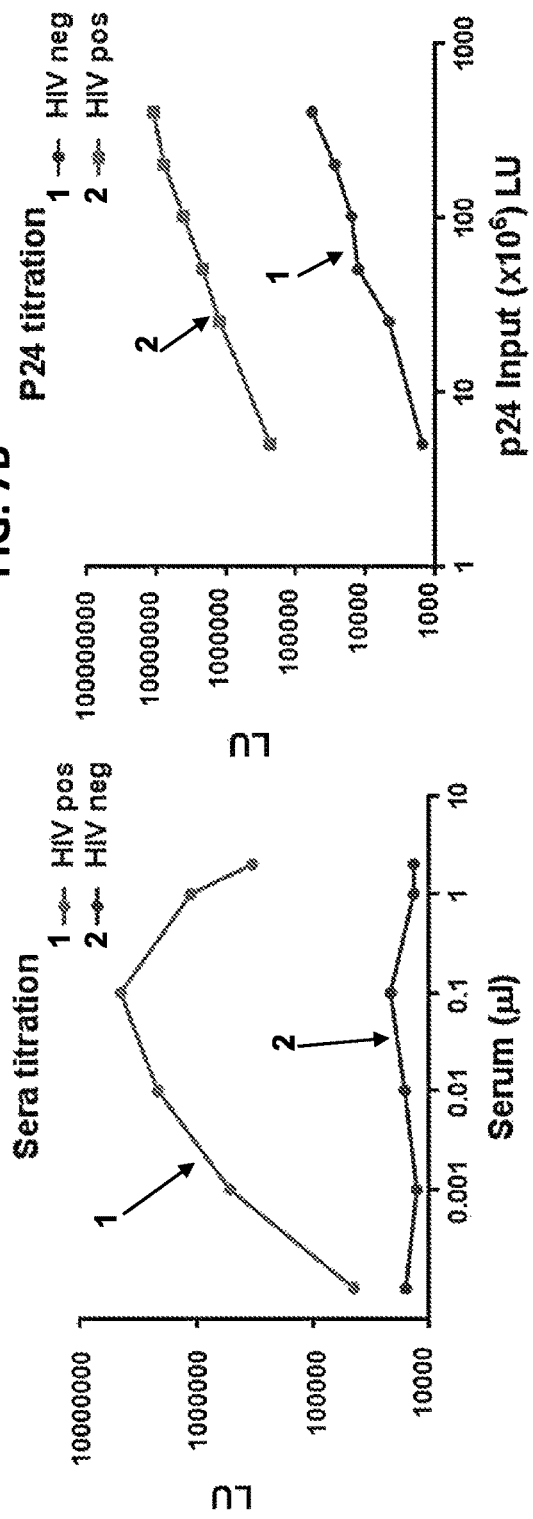
Figure 10:
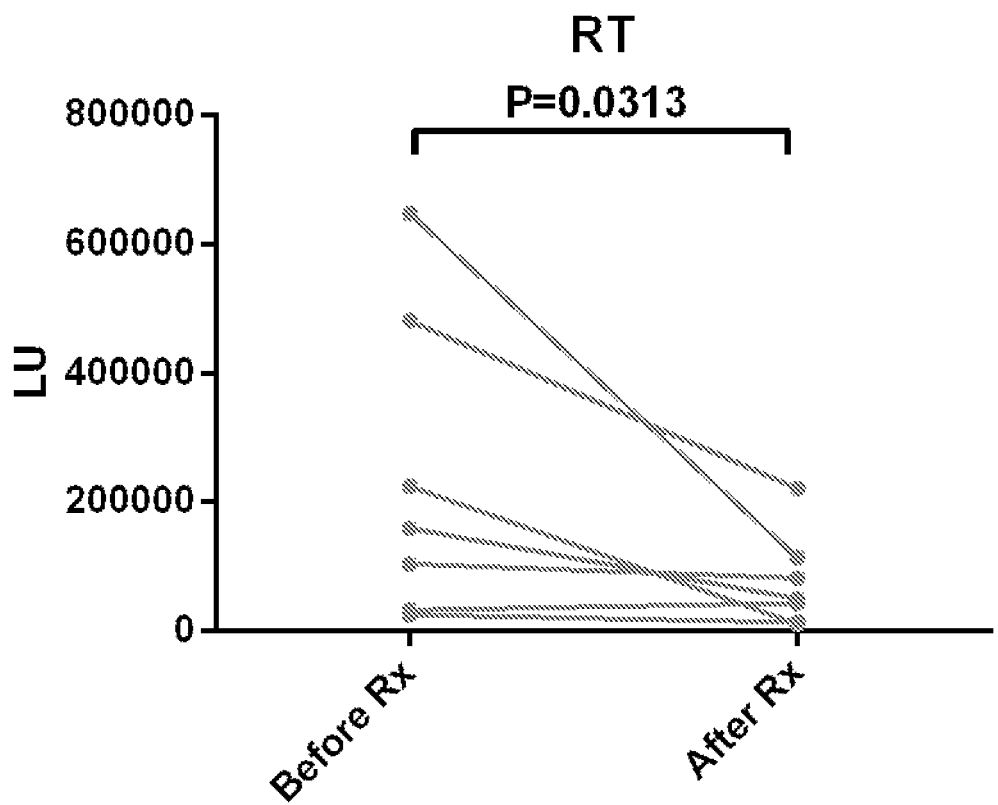
FIG. 10 is a graph showing the results of LIPSTICKS HIV reverse transcriptase antibody detection in seven HIV subjects from before and after 4-5 years of anti-retroviral therapy. A Wilcoxon matched-pairs signed rank test showed a statistically significant decrease in RT antibodies with treatment.
Figure 11:
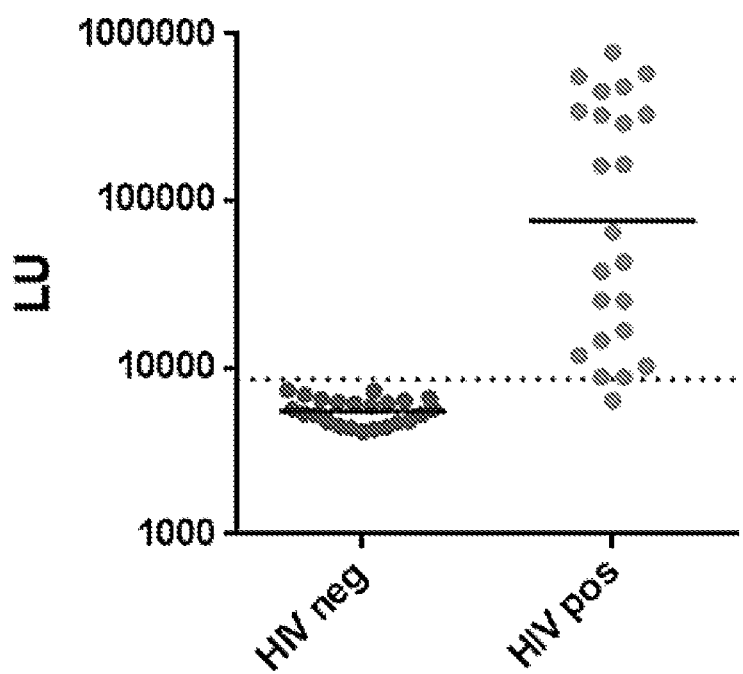
FIG. 11 is a graph showing the results of LIPSTICKS HIV p24 antibody detection in a cohort of HIV negative and HIV positive individuals. The geometric mean in each group is shown by the horizontal bar and the cut-off value for seropositivity is shown by the dotted line.

To evaluate the performance of LIPSTICKS for sensitivity and specificity, a luciferase-HIV reverse transcriptase (RT) antigen (Burbelo et al., *J Infect Dis* 209(10):1613-1617, 2014) was used in the assay with a cohort of uninfected (n=24) and HIV-infected patient serum samples (n=24). As shown in FIG. 7C, the geometric mean level of antibodies in the HIV-infected samples was 291,000 LU (95% CI 180,100-470,000), 78-fold higher than the uninfected controls, where the value was 3,742 LU (95% CI 3417-4099). This rapid testing was highly reproducible with a coefficient of variation 16%±3%. The mean of the controls plus three standard deviations was used as a cutoff value, which revealed 100% (28/28) sensitivity and 100% specificity for HIV diagnosis. Additional rapid testing of serum samples from before and after long term anti-retroviral treated HIV patients showed a statistically significant drop in anti-RT antibody levels (FIG. 10), which previously was not observed using the standard LIPS format (Burbelo et al., *J Infect Dis* 209(10):1613-1617, 2014). These results suggest that the rapid, non-equilibrium conditions of LIPSTICKS are useful for monitoring antibody changes associated with HIV treatment. Lastly, analysis with a luciferase-HIV p24 capsid fusion protein as probe, an antigen known to have lower diagnostic sensitivity than HIV RT, demonstrated 96% sensitivity and 100% specificity (FIG. 11).

Figure 7D:
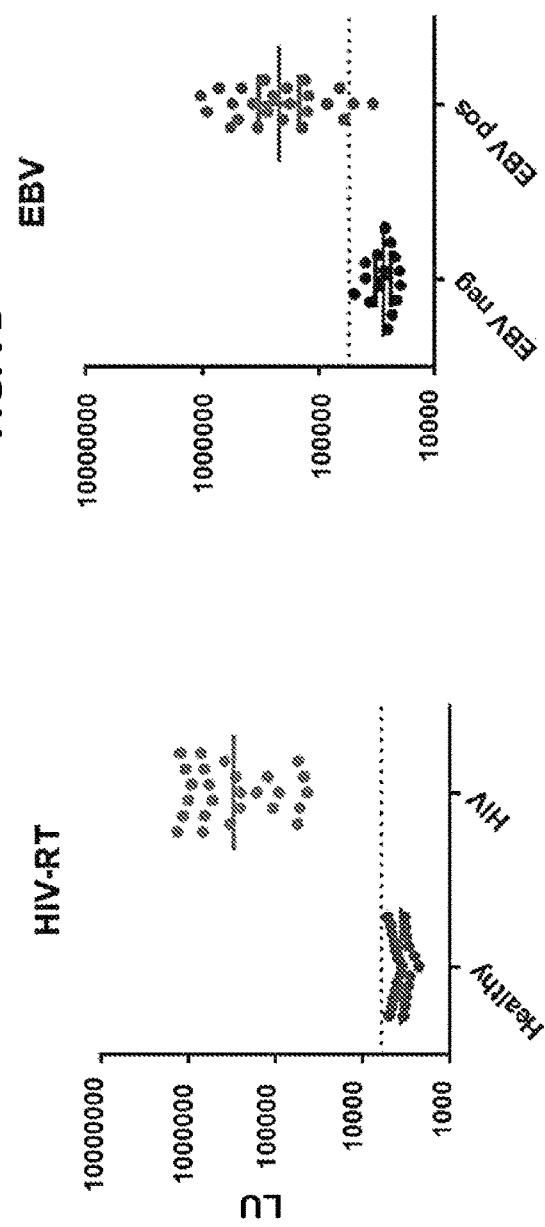
Figure 12:
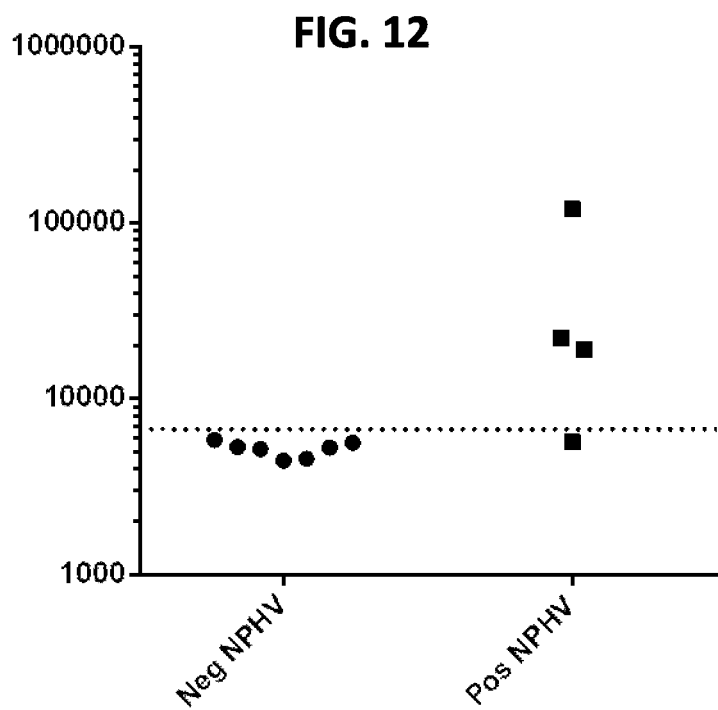
FIG. 12 is a graph showing the results of LIPSTICKS detection of antibodies against equine non-primate hepacivirus (NPHV) in seronegative (circles) and seropositive (squares) horse serum samples. The cut-off value for seropositivity is shown by the dotted line.

Disease-related antibodies were evaluated by LIPSTICKS for two additional infectious diseases. First, a luciferase-EBNA fusion protein (Bu et al., *Clin Vaccine Immunol* 23(4):363-369, 2016) was utilized in a cohort of seronegative and seropositive EBV human serum samples. Compared to a VCA EBV ELISA, two positive samples were not detected by LIPSTICKS (FIG. 7D). However, two other ELISA negative samples were positive by LIPSTICKS and additional testing confirmed them as true EBV positives (FIG. 7D). Thus, the one minute assay produced results with 92% sensitivity and 100% specificity and showed identical diagnostic performance to an ELISA, which requires several hours for completion. Additionally, LIPSTICKS was used for a potential veterinary application, the serological detection of equine nonprimate hepacivirus virus (NPHV) infection (Burbelo et al., *J Virol* 86(11):6171-6178, 2012). As shown in FIG. 12, a luciferase-NHPV helicase antigen fusion detected seropositive horse serum samples and produced results similar to the standard LIPS assay.

The efficacy of LIPSTICKS for the detection of autoantibodies in several autoimmune diseases was also assessed. First, anti-interferon-γ autoantibodies were examined, which are associated with an acquired immune condition often characterized by non-tuberculosis mycobacterial infection (Browne et al., *N Engl J Med* 367(8):725-734, 2012). Similar to previous results with the standard LIPS assay, ultrarapid testing with neodymium magnets showed 95% sensitivity and 100% specificity (FIG. 8A). Next, autoantibodies against BPIFB1, a secreted protein, which have been reported to be associated with interstitial lung disease in patients with autoimmune polyendocrinopathy-candidiasis-ectodermal dystrophy (APECED) were evaluated (Shum et al., *Sci Transl Med* 5(206):206ra139, 2013). For these studies, a *Gaussia* luciferase reporter, which expresses better for secreted proteins, was fused to the C-terminus of BPIFB1. Testing by LIPSTICKS with the BPIFB1-*Gaussia* luciferase fusion protein showed 95% sensitivity and 100% specificity in the cohort compared to the standard 2.5 hour LIPS assay (FIG. 8B).

Sjögren's syndrome (SS) involves chronic inflammation and autoimmune attack on the salivary and lacrimal glands resulting in the loss of saliva and tear production, respectively (Fox, *Lancet* 366(9482):321-331, 2005). Autoantibodies against SSA, composed of the Ro52 and Ro60 proteins, and SSB (La protein), are present in a subset of patients with of SS (Burbelo et al., *Autoimmunity* 42(6):515-24, 2009). It has been previously shown that saliva can be used in LIPS for the assessment of autoantibody levels in SS (Ching et al., *J Dent Res* 90(4):445-449, 2011). Due to the simplicity of collecting saliva directly, a cohort of saliva samples (10 µL) from healthy volunteers (n=18) and SS patients (n=17) was tested. The results were compared serum testing of these same subjects based on clinical diagnosis and SSA ELISA data measuring both Ro52 and Ro60 together. As shown in FIG. 8C, the *Renilla* luciferase-Ro60 saliva LIPSTICKS test had 70% sensitivity (100% specificity) for SS diagnosis and showed identical results with the serum ELISA test. The *Renilla* luciferase-Ro52 saliva LIPSTICKS test on the same samples was less informative with 53% sensitivity (100% specificity) for SS diagnosis (FIG. 8D). These results demonstrate that saliva is a practical clinical sample for use in a one minute Ro60 autoantibody test for the diagnosis of Sjögren's syndrome.

Figure 8E:
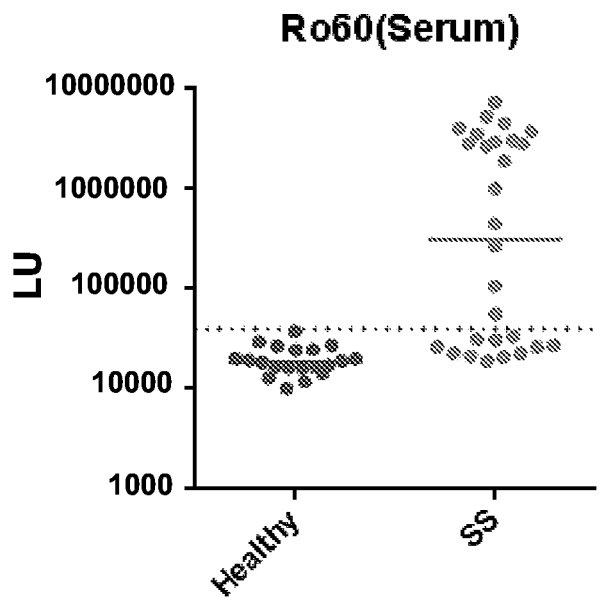
Figure 13:
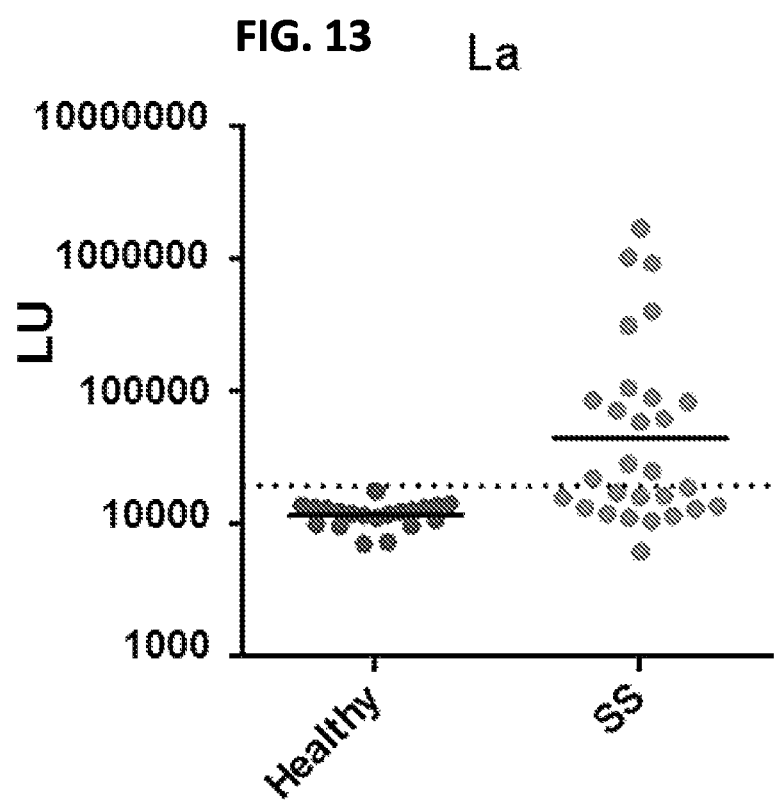
FIG. 13 is a graph showing the results of LIPSTICKS La autoantibody detection in a cohort of normal volunteers and Sjögren's syndrome patients. The geometric mean in each group is shown by the horizontal bar and the cut-off value for seropositivity is shown by the dotted line.

LIPSTICKS was also performed with a different cohort of serum samples from healthy controls and SS patients using *Renilla* luciferase-Ro60 and *Renilla* luciferase-La autoantigen extracts and the results were compared with clinical ELISA data. As shown in FIG. 8E, much higher LU values for Ro60 autoantibodies were observed in the SS cohort compared to the healthy controls, yielding 59% ($^{17}/_{29}$) sensitivity and 100% specificity and produced identical results with the conventional ELISA. The SSB/La, known to have lower diagnostic sensitivity (Burbelo et al., *Autoimmunity* 42(6):515-24, 2009), also showed promising results by LIPSTICKS with 52% sensitivity and 100% specificity and picked up two additional positives missed by the ELISA (FIG. 13).

Figure 8F:
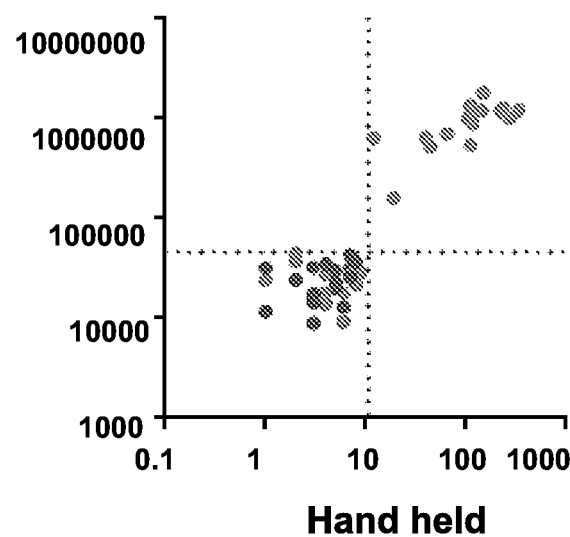

To extend the LIPSTICKS technique into portable antibody testing, a handheld, battery operated luminometer designed for ATP-based assaying of bacterial contamination was utilized (Omidbakhsh et al., *PLoS One* 9(6):e99951, 2014). Initial calibration experiments with the handheld luminometer revealed that the light output generated by the *Renilla* luciferase-antigen flash with coelenterazine substrate or even a glow *Renilla* substrate was insufficiently detected by the photodiode detector. To enhance the luciferase signal, a different luciferase (NANOLUC™) was used, which has a sustained glow and higher specific activity (Hall et al., *ACS Chem Biol* 7(11):1848-1857, 2012). Ro52-NANOLUC™ extract in the LIPSTICKS assay with healthy volunteer and SS patient sera produced values by the handheld luminometer that tracked those obtained with the tube luminometer and produced results that matched the ELISA (FIG. 8F). These findings indicate that LIPSTICKS is capable of being used with a portable device.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A method for detecting antigen-specific antibodies in a biological fluid sample, comprising:
   (i) providing a fusion protein comprising an antigen fused to a luciferase protein;
   (ii) contacting the biological fluid sample with the fusion protein, thereby forming immune complexes if antigen-specific antibodies are present in the biological fluid sample;
   (iii) contacting the immune complexes with magnetic beads coated with an immunoglobulin-binding protein to form bead-bound immune complexes;
   (iv) isolating the bead-bound immune complexes by directly contacting the bead-bound immune complexes with a neodymium magnet; and
   (v) detecting emission of light from the isolated bead-bound immune complexes, thereby detecting the presence of antigen-specific antibodies in the biological fluid sample.

2. The method of claim 1, wherein the biological fluid sample comprises serum, plasma, blood, urine, saliva or bronchoalveolar lavage fluid.

3. The method of claim 1, wherein the total volume of the biological fluid sample is no more than 2 µL.

4. The method of claim 1, wherein the biological fluid sample comprises saliva and the total volume of the biological sample is no more than 10 µL.

5. The method of claim 1, wherein the luciferase comprises a *Renilla* luciferase, a *Gaussia* luciferase, a modified *Oplophorus gracilirostris* luciferase, a firefly luciferase or a bacterial luciferase.

6. The method of claim 1, wherein the immunoglobulin-binding protein comprises Protein A, Protein G, Protein A/G, Protein L or a secondary antibody.

7. The method of claim 1, wherein the magnet is rod-shaped and has a diameter of about 1/16 inch to about 3/16 inch.

8. The method of claim 7, wherein the magnet has a diameter of about 1/16 inch or about 1/8 inch.

9. The method of claim 1, wherein:
   step (ii) is performed for a minimum of 30 seconds to a maximum of 2 minutes;
   step (iii) is performed for a minimum of 30 seconds to a maximum of 4 minutes;
   step (iv) is performed for a maximum of 15 seconds; or any combination thereof.

10. The method of claim 1, wherein the emission of light is detected using a luminometer.

11. The method of claim 1, wherein the antibodies are autoantibodies.

12. The method of claim 11, wherein the autoantibodies are antibodies specific for Ro52, Ro60 or La.

13. The method of claim 11, wherein the autoantibodies are antibodies specific for interferon-γ.

14. The method of claim 11, wherein the autoantibodies are antibodies specific for BPI fold containing family B, member 1 (BPIFB1).

15. The method of claim 1, wherein the antibodies are pathogen-specific antibodies.

16. The method of claim 15, wherein the pathogen is a viral pathogen, a bacterial pathogen, a fungal pathogen or a parasite.

17. The method of claim 16, wherein:
   the viral pathogen is human immunodeficiency virus (HIV) and the antibodies are specific for HIV p24 or reverse transcriptase;
   the viral pathogen is Epstein-Barr virus (EBV) and the antibodies are specific for EBV nuclear antigen 1 (EBNA1);
   or the viral pathogen is equine non-primate hepacivirus (NPHV) and the antibodies are specific for NPHV helicase.

* * * * *